US006255064B1

(12) United States Patent
Tindal et al.

(10) Patent No.: US 6,255,064 B1
(45) Date of Patent: Jul. 3, 2001

(54) DISINTEGRIN METALLOPROTEASE AND ITS USE

(75) Inventors: Michael Howard Tindal, Wyoming; Tariq Mehmood Haqqi, Cleveland Heights, both of OH (US)

(73) Assignees: The Procter & Gamble Company, Mason; Case Western Reserve University, Cleveland, both of OH (US)

( * ) Notice: Subject to any disclaimer, the term of this patent is extended or adjusted under 35 U.S.C. 154(b) by 0 days.

(21) Appl. No.: 09/030,335

(22) Filed: Feb. 25, 1998

Related U.S. Application Data

(63) Continuation-in-part of application No. PCT/US97/03217, filed on Feb. 28, 1997, and a continuation-in-part of application No. 08/810,153, filed on Feb. 25, 1997, now abandoned.
(60) Provisional application No. 60/012,679, filed on Mar. 1, 1996.

(51) Int. Cl.⁷ .............................. C12Q 1/37; C12N 9/50; C12N 9/64
(52) U.S. Cl. .............................. 435/23; 435/219; 435/226
(58) Field of Search ................................. 435/219, 226, 435/23

(56) References Cited

U.S. PATENT DOCUMENTS

| 4,683,195 | 7/1987 | Mullis et al. | 435/6 |
|---|---|---|---|
| 4,683,202 | 7/1987 | Mullis et al. | 435/91 |
| 5,922,546 | * 1/1999 | Mayer et al. | 435/6 |
| 5,935,792 | 8/1999 | Rubin et al. | 435/6 |
| 6,013,466 | * 1/2000 | Black et al. | 435/23 |

FOREIGN PATENT DOCUMENTS

| WO 96/41624 | 12/1996 | (WO) . |
|---|---|---|
| WO 97/31931 | 9/1997 | (WO) . |

OTHER PUBLICATIONS

G.M. McGeehan, et al., "Regulation of Tumour Necrosis Factor–α Processing by a Metalloproteinase Inhibitor", *Nature*, vol. 370, pp. 568–561, (1994).
L. Howard, et al., "Molecular Cloning of MADM: A Catalytically Active Mammalian Disintegrin–Metalloprotease Expressed in Various Cell Types", *Biochem. J.*, vol. 317, pp. 45–50, (1996).
T.G. Wolfsberg, et al., "ADAM, a Novel Family of Membrane Proteins Containing A Disintegrin And Metalloprotease Domain: Multipotential Functions in Cell–Cell and Cell–Matrix Interactions", *J. of Cell Biology*, vol. 131, No. 2, pp. 275–278, (1995).

G. Weskamp, et al., "MCD9, a Widely Expressed Cellular Disintegrin Containing Cytoplasmic Ligand Domains", *J. of Cell Biology*, vol. 132, No. 4, pp. 717–726 (1996).
J. Kratzschmar, et al., "Metargidin, a Membrance–anchored Metalloprotease–Disintegrin Protein with an RGD Integrin Binding Sequence", *J. of Biolog. Chem.* vol. 271, No. 9, pp. 4593–4596 (1996).
Blobel, et al., "Genbank ACC. No. U41767", *J. Biol. Chem.*, 271 (9), pp. 4593–4596, (1996).
Blobel, et al., "Genbank ACC. No. U41766", *J. Cell. Biol.*, 132 (4), pp. 717–726, (1996).
Flannery, et al., "Genbank ACC. No. AF069645", *Matrix Biol.*, 18 (3), pp. 225–237, (1999).
Mitchell, et al., "Genbank ACC. No. Z48444", *Biochem. J.*, 317 (Pt1), pp. 45–50, (1996).
Glynn, et al., "Genbank ACC. No. Z21961", *Biochem. J.*, 317 (Pt1), pp. 45–50, (1996).
Lu, et al., "Genbank ACC. No. Z48579", *Biochem. J.*, 317, (Pt1), pp. 45–50, (1996).
Katagiri, et al., "Genbank ACC. No. D31872", *J. Cytogenet. Cell Genet.*, 68 (1–2), pp. 39–44, (1995).
A.B. Studencki, et al., "Allele–Specific Hybridization Using Oligonucleotide Probes of Very High Specific Activity: Discrimination of the Human $\beta^A$– and $\beta^S$– Globin Genes", *DNA*, vol. 3, No. 1, pp. 7–15. (1984).
R.B. Wallace, et al., "Application of Synthetic Oligonucleotides to the Diagnosis of Human Genetic Diseases", *Biochemie*, vol. 67, pp. 755–762, (1985).
M.J. Duffy, et al, "Assay of Matrix Metalloproteases types 8 and 9 by ELISA in Human Breast Cancer", *Br. J. Cancer*, vol. 71, pp. 1025–1028, (1995).
D. Fambrough, et al., "The Cell Surface Metalloprotease/ Disintegrin Kuzbanian is Required for Axonal Extension in Drosophila", *Proc. Natl. Acad. Sci. USA*, vol. 93, pp. 13233–13238, (1996).
S.E. Whitham, et al., "Comparison of Human Stromelysin and Collagenase by Cloning and Sequence Analysis", *Biochem. J.*, vol. 240, pp. 913–916. (1986).
J. Saus, et al., "The Complete Primary Structure of Human Matrix Metalloproteinase–3", *J. of Biological Chemisry*, vol. 263, No. 14, pp. 6742–6745, (1988).
S. Lammich, et al., "Constitutive and Regulated α–secretase Cleavage of Alzheimer's Amyloid Precusor Protein by a Disintegrin Metalloprotease", *Proc. Natl. Acad. Sci. USA*, vol. 96, pp. 3922–3927, (1999).

(List continued on next page.)

*Primary Examiner*—Elizabeth Slobodyansky

(57) ABSTRACT

Proteins comprising the amino acid sequence of human disintegrin and DNA sequences encoding the human disintegrin protein are identified. Also described are methods for determining the activity of the disintegrin and for identifying compounds capable of binding to and inhibiting the disintegrin protein. Recombinant expression vectors comprising the DNA sequences encoding the disintegrin, host cells comprising the recombinant expression vector, and antibodies to the disintegrin protein and screening methods for detecting levels of disintegrin protein are exemplified.

3 Claims, No Drawings

OTHER PUBLICATIONS

A. Chantry, et al., "Degradation of Myelin Basic Protein by a Membrane–Associated Metalloprotease: Neural Distribution of the Enzyme", *Neurochemical Research*, vol. 17, No. 9, pp. 861–868, (1992).

A.B. Studencki, et al., "Discrimination among the Human $\beta^A$, $\beta^S$, and $\beta^C$– Globin Genes Using Allele–Specific Oligonucleotide Hybridization Probes", *Am. J. Hum. Genet.*, vol. 37, pp. 42–51, (1985).

J. Arribas, et al., "Diverse Cell Surface Protein Ectodomains are Shed by a System Sensitive to Metalloprotease Inhibitors", *J. of Biological Chemistry*, vol. 271, No. 19, pp. 11376–11382, (1996).

R. Reich, et al., "Effects of Inhibitors of Plasminogen Activator, Serine Proteinases, and Collagenase IV on the Invasion of Basement Membranes by Metastatic Cells", *Cancer Research*, vol. 48, pp. 3307–3312, (1988).

G.I. Goldberg, et al., "Human Fibroblast Collagenase", *J. of Biological Chemistry*, vol. 261, No. 14, pp. 6600–6605, (1986).

M.S. Rodendahl, et al., "Identification and Characterization of a Pro–tumor Necrosis Factor–α–processing Enzyme from the ADAM Family of Zinc Metalloproteases", *J. of Biological Chemistry*, vol. 272, No. 39, pp. 24588–24593, (1997).

J. Rooke, et al., "KUZ, a Conserved Metalloprotease–Disintegrin Protein with Two Roles in Drosophila Neurogenesis", *Science*, vol. 273, pp. 1227–1231, (1996).

D. Pan, et al., "Kuzbanian Controls Proteolytic Processing of Notch and Mediates Lateral Inhibition during Drosophila and Vertebrate Neurogenesis", *Cell*, vol. 90, pp. 271–280, (1997).

L. Howard, et al., "Membrane–Associated Metalloproteinase Recognized by Characteristic Cleavage of Myelin Basic Protein: Assay and Isolation", *Res. Methods Neurochem.*, vol. 2, No. 219, pp. 388–395, (1974).

A. Chantry, et al., "Metalloendoprotease Cleavage of 18.2– and 14.1–Kilodalton Basic Proteins Dissociating from Rodent Myelin Membranes Generates 10.0– and 5.9–Kilodalton C–Terminal Fragments", *J. of Neurochemistry*, vol. 50, No. 3, pp. 688–694, (1988).

C.P. Biobel, Metalloprotease–Disintegrins: Links to Cell Adhesion and Cleavage of TNFα and Notch, *Cell*, vol. 90, pp. 589–592, (1997).

L. Howard, et al., "Molecular Cloning of MADM: a Catalytically Active Mammalian Disintegrin–Metalloprotease Expressed in Various Cell Types", *Biochem. J.*, vol. 317, pp. 45–50, (1996).

N. Groome, et al., "A New Epitope on Human Myelin Basic Protein Arising from Cleavage by a Metalloendoprotease Associated with Brain Myelin Membranes", *J. of Neuroimmunology*, vol. 19, pp. 77–88, (1988).

A. Chantry, et al., "A Novel Metalloproteinase Originally Isolated from Brain Myelin Membranes is Present in Many Tissues", *Biochem. J.*, vol. 268, pp. 245–248, (1990).

H. Qi, et al., "Processing of the Notch Ligand Delta by the Metalloprotease Kuzbanian", *Science*, vol. 283, pp. 91–94, (1999).

J. Marmur, et al., "Stand Sepatation and Specific Recombination in Deoxyribonucleic Acids: Biological Studies", *Biochemistry*, vol. 46, pp. 455–461, (1960).

P. Doty, et al., "Strand Separation and Specific Recombination in Deoxyribonucleic Acids: Physical and Chemical Studies", *Biochemistry*, vol. 46, pp. 461–476, (1960).

* cited by examiner

DISINTEGRIN METALLOPROTEASE AND ITS USE

This application is a continuation-in-part of U.S. application Ser. No. 08/810,153, filed Feb. 25, 1997, now abandoned, and a CIP of International Application No. PCT/US97/03217, filed Feb. 28, 1997, which claims the benefit of U.S. Provisional Application No. 60/012,679, filed Mar. 1, 1996.

FIELD OF THE INVENTION

The invention relates to a novel protein, its fragments and mutants and to its use in detecting and testing drugs for ailments, including osteoarthritis and others characterized by up regulation of metalloproteases.

BACKGROUND

A number of enzymes effect the breakdown of structural proteins and are structurally related metalloproteases. These include human skin fibroblast collagenase, human skin fibroblast gelatinase, human sputum collagenase and gelatinase, and human stromelysin. See e.g., S. E. Whitham et al., Comparison of human stromelysin and collagenase by cloning and sequence analysis" *Biochem J.* 240:913 (1986). See also G. I. Goldberg et al., "Human Fibroblast Collagenase" *J. Biol. Chem.* 261:660 (1986). Metal dependence (e.g., zinc) is a common feature of these structurally related enzymes known as "metalloproteases."

Controlled production and activity of these enzymes plays an important role in the normal development of tissue architecture. In excess, however, these enzymes can cause pathologic destruction of connective tissues. See generally, J. Saus et al., "The Complete Primary Structure of Human Matrix Metalloprotease-3" *J. Biol. Chem.* 263:6742 (1988). Many of these are zinc-containing metalloprotease enzymes, as are the angiotensin-converting enzymes and the enkephalinases. Collagenase, stromelysin and related enzymes are important in mediating the symptomatology of a number of diseases, including rheumatoid arthritis (Mullins, D. E., et al., Biochim Biophys Acta (1983) 695:117–214); osteoarthritis (Henderson, B., et al., Drugs of the Future (1990) 15:495–508); the metastasis of tumor cells (ibid, Broadhurst, M. J., et al., European Patent Application 276,436 (published 1987), Reich, R., et al., 48 Cancer Res 3307–3312 (1988); and various ulcerated conditions. Ulcerative conditions can result in the cornea as the result of alkali burns or as a result of infection by *Pseudomonas aeruginosa*, Acanthamoeba, *Herpes simplex* and vaccinia viruses.

In fact, measurement of metalloproteases in cancer tissue suggests increased levels of metalloproteases correlate with metastatic potential. See e.g., M. J. Duffy et al., "Assay of matrix metalloproteases types 8 and 9 by ELISA in human breast cancer" *Br. J. Cancer* 71:1025 (1995).

Other conditions characterized by undesired metalloprotease activity include periodontal disease, epidermolysis bullosa and scleritis. In view of the involvement of metalloproteases in a number of disease conditions, attempts have been made to prepare inhibitors to these enzymes. A number of such inhibitors are disclosed in the literature. The invention seeks to provide novel inhibitors, preferably specific to this protease, that have enhanced activity in treating diseases mediated or modulated by this protease.

Inhibitors of metalloproteases are useful in treating diseases caused, at least in part, by breakdown of structural proteins. A variety of inhibitors have been prepared, but there is a continuing need for metalloprotease inhibitor screens to design drugs for treating such diseases.

Given the involvement of matrix metalloproteases in a number of disease conditions, attempts have been made to identify inhibitors of these enzymes. For Example TapI-2 and 1,10-phenanthroline are known metalloprotease inhibitors. See, e.g., J. Arribas et al., "Diverse Cell Surface Protein Ectodomains Are Shed by a System Sensitive to Metalloprotease Inhibitors", J. Biol. Chem. 271:11376 (1996).

Metalloproteases are a broad class of proteins which have widely varied functions. Disintegrins are zinc metalloproteases, abundant in snake venom. Mammalian disintegrins are a family of proteins with about 18 known subgroups. They act as cell adhesion disrupters and are also known to be active in reproduction (for example, in fertilization of the egg by the sperm, including fusion thereof, and in sperm maturation).

These proteases and many others are uncovered in molecular biology and biochemistry. As a result, GenBank, a repository for gene sequences, provides several sequences of metalloproteases, including some said to encode fragments of disintegrins. For example, GenBank accession # Z48444 dated Feb. 25, 1994 discloses 2407 nucleotides of a rat gene said to be a rat disintegrin metalloprotease gene; GenBank accession # Z48579 dated Mar. 2, 1995 discloses 1824 nucleotides of a partial sequence of a gene said to be a human disintegrin metalloprotease gene; GenBank accession # Z21961 dated Oct. 25, 1994, discloses 2397 nucleotides of a partial sequence of a gene said to be a bovine zinc metalloprotease gene.

Because there is such a wide variety of metalloproteases, there is a continuing need for i) methods that will specifically detect a particular metalloprotease, as well as ii) methods for identifying candidate inhibitors.

It would be advantageous to implicate metalloproteases in specific disease states, and to use these metalloproteases as tools to detect and ultimately cure, control or design cures for such diseases.

OBJECTS OF THE INVENTION

It is an object of the present invention to provide a method for identifying compounds capable of binding to the disintegrin protein.

It is also an object of the present invention to provide a host cell comprising a recombinant expression vector to the disintegrin protein and a recombinant expression vector encoding to the disintegrin protein.

It is also an object of the present invention to provide a method for screening for metalloprotease mediated diseases such as cancer, arthropothies (including ankylosing spondolytis, rheumatiod arthritis, gouty arthritis (gout), inflammatory arthritis, Lyme disease and osteoarthrtis).

It is also an object of the present invention to provide an antibody to the protein useful in the screen, in the isolation of the protein or as a targeting moiety for the protein.

SUMMARY OF THE INVENTION

This invention provides a method for identifying compounds capable of binding to the disintegrin protein, and determining the amount and affinity of a compound capable of binding to the disintegrin protein in a sample.

This invention also provides a host cell comprising a recombinant expression vector to the disintegrin protein and a recombinant expression vector encoding to the disintegrin protein and the human disintegrin metalloprotease protein, fragment or mutant thereof, useful for these purposes.

This invention also provides an in vivo or in vitro method for screening for osteoarthritis and other metalloprotease based diseases, such as cancer, capable of manufacture and use in a kit form.

DETAILED DESCRIPTION

The term "gene" refers to a DNA sequence that comprises control and coding sequences necessary for the production of a mature protein or precursor thereof. The protein can be encoded by a full length coding sequence or by any portion of the coding sequence so long as the desired enzymatic activity is retained.

The term "oligonucleotide" as used herein is defined as a molecule comprised of two or more deoxyribonucleotides or ribonucleotides, usually more than three (3), and typically more than ten (10) and up to one hundred (100) or more (although preferably between twenty and thirty). The exact size will depend on many factors, which in turn depends on the ultimate function or use of the oligonucleotide. The oligonucleotide may be generated in any manner, including chemical synthesis, DNA replication, restriction endonuclease digestion reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

"Hybridization" methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, *Proc. Natl. Acad. Sci. USA* 46:453 (1960) and Doty et al., *Proc. Natl. Acad. Sci. USA* 46:461 (1960) have been followed by the refinement of this process into an essential tool of modern biology. Nonetheless, a number of problems have prevented the wide scale use of hybridization as a tool in human diagnostics. Among the more formidable problems are: 1) the inefficiency of hybridization; 2) low concentration of specific target sequences in a mixture of genomic DNA; and 3) the hybridization of only partially complementary probes and targets.

With regard to efficiency, it is experimentally observed that only a fraction of the possible number of probe-target complexes are formed in a hybridization reaction. This is particularly true with short oligonucleotide probes (less than 100 bases in length). There are three fundamental causes: a) hybridization cannot occur because of secondary and tertiary structure interactions; b) strands of DNA containing the target sequence have rehybridized (reannealed) to their complementary strand; and c) some target molecules are prevented from hybridization when they are used in hybridization formats that immobilize the target nucleic acids to a solid surface.

Even where the sequence of a probe is completely complementary to the sequence of the target, i.e., the target's primary structure, the target sequence must be made accessible to the probe via rearrangements of higher-order structure. These higher-order structural rearrangements may concern either the secondary structure or tertiary structure of the molecule. Secondary structure is determined by intramolecular bonding. In the case of DNA or RNA targets this consists of hybridization within a single, continuous strand of bases (as opposed to hybridization between two different strands). Depending on the extent and position of intramolecular bonding, the probe can be displaced from the target sequence preventing hybridization.

Solution hybridization of oligonucleotide probes to denatured double-stranded DNA is further complicated by the fact that the longer complementary target strands can renature or reanneal. Again, hybridized probe is displaced by this process. This results in a low yield of hybridization (low "coverage") relative to the starting concentrations of probe and target.

With regard to low target sequence concentration, the DNA fragment containing the target sequence is usually in relatively low abundance in genomic DNA. This presents great technical difficulties; most conventional methods that use oligonucleotide probes lack the sensitivity necessary to detect hybridization at such low levels.

One attempt at a solution to the target sequence concentration problem is the amplification of the detection signal. Most often this entails placing one or more labels on an oligonucleotide probe. In the case of non-radioactive labels, even the highest affinity reagents have been found to be unsuitable for the detection of single copy genes in genomic DNA with oligonucleotide probes. See Wallace et al., *Biochimie* 67:755 (1985). In the case of radioactive oligonucleotide probes, only extremely high specific activities are found to show satisfactory results. See Studencki and Wallace, *DNA* 3:1 (1984) and Studencki et al., *Human Genetics* 37:42 (1985).

K. B. Mullis et al., U.S. Pat. Nos. 4,683,195 and 4,683,202, hereby incorporated by reference, describe a method for increasing the concentration of a segment of a target sequence in a mixture of any DNA without cloning or purification. This process for amplifying the target sequence (which can be used in conjunction with the present invention to make target molecules) consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then allowed to annealed to their complementary sequences within the target molecule. Following annealing, the primers are extended with a polymerase so as to form a new pair of complementary strands. The steps of denaturation, primer annealing, and primer extension can be repeated many times (i.e., denaturation, annealing and extension constitute one "cycle;" there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to by the inventors as the "Polymerase Chain Reaction" (hereinafter PCR). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}P$ labeled deoxynucleotide triphosphates, e.g., dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

The PCR amplification process is known to reach a plateau concentration of specific target sequences of approximately $10^{-8}$ M. A typical reaction volume is 100 μl, which corresponds to a yield of $6 \times 10^{11}$ double stranded product molecules.

With regard to complementarity, it is important for some diagnostic applications to determine whether the hybridization represents complete or partial complementarity. For example, where it is desired to detect simply the presence or absence of pathogen DNA or RNA (such as from a virus, bacterium, fungi, mycoplasma, protozoan) it is only important that the hybridization method ensures hybridization when the relevant sequence is present; conditions can be selected where both partially complementary probes and completely complementary probes will hybridize. Other diagnostic applications, however, may require that the hybridization method distinguish between partial and complete complementarity. It may be of interest to detect genetic polymorphisms. For example, human hemoglobin is composed, in part, of four polypeptide chains. Two of these chains are identical chains of 141 amino acids (alpha chains) and two of these chains are identical chains of 146 amino acids (beta chains). The gene encoding the beta chain is known to exhibit polymorphism. The normal allele encodes a beta chain having glutamic acid at the sixth position. The mutant allele encodes a beta chain having valine at the sixth position. This difference in amino acids has a profound (most profound when the individual is homozygous for the mutant allele) physiological impact known clinically as sickle cell anemia. It is well known that the genetic basis of the amino acid change involves a single base difference between the normal allele DNA sequence and the mutant allele DNA sequence.

Unless combined with other techniques (such as restriction enzyme analysis), methods that allow for the same level of hybridization in the case of both partial as well as complete complementarity are typically unsuited for such applications; the probe will hybridize to both the normal and variant target sequence. Hybridization, regardless of the method used, requires some degree of complementarity between the sequence being assayed (the target sequence) and the fragment of DNA used to perform the test (the probe). (Of course, one can obtain binding without any complementarity but this binding is nonspecific and to be avoided.)

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Stability of a nucleic acid duplex is measured by the melting temperature, or "$T_m$." The $T_m$ of a particular nucleic acid duplex under specific conditions is the temperature at which on average half of the base pairs have disassociated. The equation for calculating the $T_m$ of nucleic acids is well known in the art. As indicated by strand references, an estimate of the $T_m$ value may be calculated by the equation:

$$T_m = 81.5° \text{ C.} + 16.6 \log M + 0.41(\% \ GC) - 0.61(\% \ form) - 500/L$$

where M is the molarity of monovalent cations, % GC is the percentage of guanosine and cytosine nucleotides in the DNA, % form is the percentage of formamide in the hybridization solution, and L=length of the hybrid in base pairs [See, e.g., Guide to Molecular Cloning Techniques, Ed. S. L. Berger and A. R. Kimmel, in Methods in Enzymology Vol. 152, 401 (1987)]. Other references include more sophisticated computations which take structural as well as sequence characteristics into account for the calculation of $T_m$.

The term "probe" as used herein refers to a labeled oligonucleotide which forms a duplex structure with a sequence in another nucleic acid, due to complementarity of at least one sequence in the probe with a sequence in the other nucleic acid.

The term "label" as used herein refers to any atom or molecule which can be used to provide a detectable (preferably quantifiable) signal, and which can be attached to a nucleic acid or protein. Labels may provide signals detectable fluorescence, radioactivity, colorimetry, gravimetry, X-ray diffraction or absorption, magnetism, enzymatic activity, and the like. Such labels can be added to the oligonucleotides of the present invention.

The terms "nucleic acid substrate" and nucleic acid template" are used herein interchangeably and refer to a nucleic acid molecule which may comprise single- or double-stranded DNA or RNA.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

The term "sequence variation" as used herein refers to differences in nucleic acid sequence between two nucleic acid templates. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence form both the wild-type gene and the first mutant form of the gene. It should be noted that, while the invention does not require that a comparison be made between one or more forms of a gene to detect sequence variations, such comparisons are possible with the oligo/solid support matrix of the present invention using particular hybridization conditions as described in U.S. pat. appl. Ser. No. 08/231,440, hereby incorporated by reference.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, reverse transcriptase-PCR (RT-PCRs) and the like.

A "consensus gene sequence" refers to a gene sequence which is derived by comparison of two or more gene sequences and which describes the nucleotides most often present in a given segment of the genes; the consensus sequence is the canonical sequence.

As used herein, the terms "protein" and "protease" refer to metalloprotease. The term "metalloprotease" refers to a native metal dependent protease, a fragment thereof, a mutant or homologue which still retains its function. The invention contemplates metalloproteases (or "disintegrins") from differing species, and those prepared by recombinant methods, in vitro methods, or standard peptide synthesis. Preferably the protein is a human disintegrin or mutant thereof. For the purposes of defining the mutants of the protein the preferred "native" protein is partially described in Gen Bank accession #Z48579, incorporated herein by reference and referred to in the sequence below. Homologue disintegrins include whole proteins with at least 90% homology as understood by the art, or fragments thereof. It is recognized that some interspecies variation may occur including insertions or deletions which may or may not alter function. For example, a rat protein which is 95% homologous to the protein based on the peptide sequence, and a bovine protein (based on DNA sequence) being 97–98% homologous based on the first 300 base pairs are both considered homologues. For reference GenBank accession #Z48444 dated Feb. 25, 1994 discloses 2407 bases of a rat gene said to be a rat disintegrin metalloprotease gene; GenBank accession #Z21961 dated Oct. 25, 1994, discloses 2397 bases of a partial sequence of a gene said to be a bovine zinc metalloprotease gene. Preferably this metalloprotease is a human disintegrin as described below.

The term "antibody" refers to an antibody to a disintegrin, or fragment thereof. These many be monoclonal or polyclonal, and can be from any of several sources. The invention also contemplates fragments of these antibodies made by any method in the protein or peptide art.

The term "disease screen" refers to a screen for a disease or disease state. A disease state is the physiological or cellular or biochemical manifestation of the disease. Preferably this screen is used on body tissues or fluids of an animal or cell culture, using standard techniques, such as ELISA. It also contemplates "mapping" of disease in a whole body, such as by labeled antibody as described above given systemically: regardless of the detection method, preferable such detection methods include fluorescence, X-ray (including CAT scan), NMR (Including MRI), and the like.

The term "compound screen" is related to the methods and screens related to finding compounds, determining their affinity for the protease, or designing or selecting compounds based on the screen. In another embodiment, it contemplates the use of the three dimensional structure for drug design, preferable "rational drug design", as understood by the art. It may be preferred that the protease is in "essentially pure form", which refers to a protein reasonably free of other impurities, so as to make it useful for experiments or characterization. Use of this screening method assists the skilled artisan in finding novel structures, whether made by the chemist or by nature, which bind to and preferably inhibit the protease. These "inhibitors" may be useful in regulating or modulating the activity of the protease, and may be used to thus modulate the biological cascade that they function in. This approach affords new pharmaceutically useful compounds.

The term "disintegrin" refers to a disintegrin, a fragment thereof, a mutant thereof or a homologue which still retains its function. This term contemplates aggrecanase, and other proteases which are involved in or modulate tissue remodeling. This contemplates disintegrins from differing species, and those prepared by recombinant methods, in vitro methods, or standard peptide synthesis. Preferably the protein is a human disintegrin or mutant thereof. For the purposes of defining the mutants, with reference to a protein is partially described in GenBank accession # Z48579, incorporated herein by reference and referred to in the sequence below. SEQ ID NO:1 describes a fragment of that DNA sequence and its transcript and SEQ ID NO:2 describes the protein coded by the gene. Homologue disintegrins include whole proteins with at least 90% homology as understood by the art, or fragments thereof. For example, a rat protein which is 95% homologous to that of SEQ ID NO:2 based on the amino acid sequence derived from the DNA or cDNA sequence containing SEQ ID NO:1, and a bovine protein (similarly derived) being 97–98% homologous, are both considered homologues. Thus homologous cDNAs cloned from other organisms give rise to homologous proteins.

Likewise proteins may be considered homologues based on the amino acid sequence alone. Practical limitations of amino acid sequencing would allow one to determine that a protein is homologous to another using, for example, comparison of the first 50 amino acids of the protein. Hence 90% homology in would allow for 5 differing amino acids in the chain of the first 50 amino acids of the homologous protein.

The skilled artisan will appreciate that the degeneracy of the genetic code provides for differing DNA sequences to provide the equivalent transcript, and thus the same protein. In certain cases preparing the DNA sequence, which encodes for the same protein, but differs from the native DNA include;

ease of sequencing or synthesis;

increased expression of the protein; and preference of certain heterologous hosts for certain codons over others.

These practical considerations are widely known and provide embodiments that may be advantageous to the user of the invention. Thus it is clearly contemplated that the native DNA is not the only embodiment envisioned in this invention.

In addition it is apparent to the skilled artisan that fragments of the protein may be used in screening, drug design and the like, and that the entire protein may not be required for the purposes of using the invention. Thus it is clearly contemplated that the skilled artisan will understand that the disclosure of the protein and its uses contemplates the useful peptide fragments.

The practical considerations of protein expression, purification yield, stability, solubility, and the like, are considered by the skilled artisan when choosing whether to use a fragment, and the fragment to be used. As a result, using routine practices in the art, the artisan can, given this disclosure practice the invention using fragments of the protein as well.

Thus, the present invention specifically contemplates the use of less than the entire nucleic acid sequence for the gene and less than the entire amino acid sequence of the protein. Fragments of the protein may be used in screening, drug design and the like, and that the entire protein may not be required for the purposes of using the invention. The protein itself can be used to determine the binding activity of small molecules to the protein. Drug screening using enzymatic targets is used in the art and can be employed using automated, high throughput technologies.

The protein or protease itself can be used to determine the binding activity of small molecules to the protein. Drug screening using enzymatic targets is used in the art and can be employed using automated, high throughput technologies.

The inhibition of disintegrin activity may be a predictor of efficacy in the treatment of osteoarthritis, and other diseases involving degeneration of articular cartilage and other tissues having matrix degradation, such as tissue remodeling and the like.

Gene therapy

Without being bound by theory it is thought that the metalloprotease is up regulated during osteoarthritis in tissues. We have surprisingly found that a human disintegrin is up-regulated in human chondrocytes during osteoarthritic conditions. Inhibition of signal transduction mechanism is efficacious in disrupting the cascade of events in osteoarthritis and other diseases involving cartilage degeneration. The skilled artisan will recognize that if up-regulation is a cause of the onset of arthritis, then interfering with the activity of this gene may be useful in treating osteoarthritis.

This is done by any of several methods, including gene (i.e., antisense) therapy.

Purification of the protease

Media, cell extracts or inclusion bodies from mammalian, yeast, insect or eukaryotic cells containing recombinant disintegrin or fragments of the full length protein are used for purification of disintegrin or fragments of disintegrin. Solutions consisting of denatured disintegrin may be refolded prior to purification across successive chromatographic resins or following the final stage of separation. Media, cell extracts, or solubilized disintegrin are prepared in the presence of one or a combination of detergents, denaturants or organic solvents, such as octylglucoside, urea or dimethylsulfoxide, as required. Ion exchange and hydrophobic interaction chromatography are used individually or in combination for the separation of recombinant disintegrin from contaminating cell material. Such material is applied to the column and disintegrin is eluted by adjustment of pH, changes in ionic strength, addition of denaturant and/or use of organic solvent. Typically, solutions containing disintegrin are then passed over an antibody affinity column or ligand affinity column for site specific purification of disintegrin. The immunoaffinity column contains an antibody specific for disintegrin immobilized on a solid support such as Sepharose 4B (Pharmacia) or other similar materials. Preferably, the column is washed to remove unbound proteins and the disintegrin is eluted via low pH glycine buffer or high ionic strength. The ligand affinity column may have specificity for the active site of disintegrin or to a portion of the molecule adjacent or removed from the active site. The column is washed and disintegrin is eluted by addition of a competing molecule to the elution buffer. Preferably, a protease inhibitor cocktail containing one or more protease inhibitors, such as benzamidine, leupeptin, phosphoramidon, phenylmethylsulfonyl fluoride, and 1,10-phenanthroline is present throughout the purification procedure. Various detergents such as octylthioglucoside and Triton X-100 or chemical agents such as glycerol may be added to increase disintegrin solubility and stability. Final purification of the protein is achieved by gel filtration across a chromatographic support, if required.

Inhibitors of the protease

The protease of the invention can be used to find inhibitors of the protease. Hence it is useful as a screening tool or for rational drug design. Without being bound by theory, the protease may modulate cellular remodeling and in fact may enhance extracellular matrix remodeling and thus enhance tissue breakdown. Hence inhibition of disintegrin provides a therapeutic route for treatment of diseases characterized by these processes.

In screening, a drug compound can be used to determine both the quality and quantity of inhibition. As a result such screening provides information for selection of actives, preferably small molecule actives, which are useful in treating these diseases.

In therapy, inhibition of disintegrin metalloprotease activity via binding of small molecular weight, synthetic metalloprotease inhibitors, such as those used to inhibit the matrix metalloproteases would be used to inhibit extracellular matrix remodeling.

Antibodies to the protein

Metalloproteases can be targeted by conjugating a metalloprotease inhibitor to a to an antibody or fragment thereof. Conjugation methods are known in the art. These antibodies are then useful both in therapy and in monitoring the dosage of the inhibitors.

The antibody of the invention can also be conjugated to solid supports. These conjugates can be used as affinity reagents for the purification of a desired metalloprotease, preferably a disintegrin.

In another aspect, the antibody of the invention is directly conjugated to a label. As the antibody binds to the metalloprotease, the label can be used to detect the presence of relatively high levels of metalloprotease in vivo or in vitro cell culture.

For example, targeting ligand which specifically reacts with a marker for the intended target tissue can be used. Methods for coupling the invention compound to the targeting ligand are well known and are similar to those described below for coupling to carrier. The conjugates are formulated and administered as described above.

Preparation and Use of Antibodies:

Antibodies may be made by several methods, for example, the protein may be injected into suitable (e.g., mammalian) subjects including mice, rabbits, and the like. Preferred protocols involve repeated injection of the immunogen in the presence of adjuvants according to a schedule which boosts production of antibodies in the serum. The titers of the immune serum can readily be measured using immunoassay procedures, now standard in the art.

The antisera obtained can be used directly or monoclonal antibodies may be obtained by harvesting the peripheral blood lymphocytes or the spleen of the immunized animal and immortalizing the antibody-producing cells, followed by identifying the suitable antibody producers using standard immunoassay techniques.

Polyclonal or monoclonal preparations are useful in monitoring therapy or prophylaxis regimens involving the compounds of the invention. Suitable samples such as those derived from blood, serum, urine, or saliva can be tested for the presence of the protein at various times during the treatment protocol using standard immunoassay techniques which employ the antibody preparations of the invention.

These antibodies can also be coupled to labels such as scintigraphic labels, e.g., Tc-99 or I-131, using standard coupling methods. The labeled compounds are administered to subjects to determine the locations of excess amounts of one or more metalloproteases in vivo. Hence a labeled antibody to the protein would operate as a screening tool for such enhanced expression, indicating the disease.

The ability of the antibodies to bind metalloprotease selectively is thus taken advantage of to map the distribution of these enzymes in situ. The techniques can also be employed in histological procedures and the labeled antibodies can be used in competitive immunoassays.

Antibodies are advantageously coupled to other compounds or materials using known methods. For example, materials having a carboxyl functionality, the carboxyl residue can be reduced to an aldehyde and coupled to carrier through reaction with side chain amino groups, optionally followed by reduction of imino linkage formed. The carboxyl residue can also be reacted with side chain amino groups using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill.

These antibodies, when conjugated to a suitable chromatography material are useful in isolating the protein. Separation methods using affinity chromatography are well known in the art, and are within the purview of the skilled artisan.

Disease marker

As noted above, the present invention contemplates detecting expression of metalloprotease genes in samples, including samples of diseased tissue. It is not intended that the present invention be limited by the nature of the source of nucleic acid (whether DNA or RNA); a variety of sources is contemplated, including but not limited to mammalian (e.g., cancer tissue, lymphocytes, etc.), sources.

Without being bound by theory, expression of genes, and preferably this gene may have a restricted tissue distribution and its expression is up regulated by potential osteoarthritis mediators. Enhanced expression of this gene (and hence its protein) for example, in articular chondrocytes provides a marker to monitor the development, including the earliest, asymptomatic stages, and the progression of osteoarthritis. Hence an antibody raised to the protein would operate a screening tool for such enhanced expression, indicating the disease.

In addition, when used in a disease screen, antibodies can be conjugated to chromophore or fluorophore containing materials, or can be conjugated to enzymes which produce chromophores or fluorophores in certain conditions. These conjugating materials and methods are well known in the art. When used in this manner detection of the protein by immunoassay is straightforward to the skilled artisan. Body fluids, (serum, urine, synovial fluid) for example can be screened in this manner for calibration, and detection of distribution of metalloproteases, or increased levels of these proteases.

When used in this way the invention is a useful diagnostic and/or clinical marker for metalloprotease mediated diseases, such as osteoarthritis or other articular cartilage degenerative diseases or other diseases characterized by degradation or remodeling of extracellular matrix. When disease is detected, it may be treated before the onset of symptom or debilitation.

Furthermore, such antibodies can be used to target diseased tissue, for detection or treatment as described above.

Nucleic Acid Derived Tools

The nucleic acid content of cells consists of deoxyribonucleic acid (DNA) and ribonucleic acid (RNA). The DNA contains the genetic blueprint of the cell. RNA is involved as an intermediary in the production of proteins based on the DNA sequence. RNA exists in three forms within cells, structural RNA (i.e., ribosomal RNA "rRNA"), transfer RNA ("tRNA"), which is involved in translation, and messenger RNA ("mRNA"). Since the mRNA is the intermediate molecule between the genetic information encoded in the DNA, and the corresponding proteins, the cell's mRNA component at any given time is representative of the physiological state of the cell. In order to study and utilize the molecular biology of the cell, it is therefore important to be able to purify mRNA, including purifying mRNA from the total nucleic acid of a sample.

The preparation of RNA is complicated by the presence of ribonucleases that degrade RNA (e.g., T. Maniatis et al., Molecular Cloning, pp. 188–190, Cold Spring Harbor Laboratory [1982]). Furthermore, the preparation of amplifiable RNA is made difficult by the presence of ribonucleoproteins in association with RNA. (See, R. J. Slater, In: *Techniques in Molecular Biology*, J. M. Walter and W. Gaastra, eds., Macmillan, N.Y., pp. 113–120 [1983]).

Typically, the steps involved in purification of nucleic acid from cells include 1) cell lysis; 2) inactivation of cellular nucleases; and 3) separation of the desired nucleic acid form the cellular debris and other nucleic acid. Cell lysis may be achieved through various methods, including enzymatic, detergent or chaotropic agent treatment. Inactivation of cellular nucleases may be achieved by the use of proteases and/or the use of strong salts. Finally, separation of the desired nucleic acid is typically achieved by extraction of the nucleic acid with phenol or phenol-chloroform; this method partitions the sample into an aqueous phase (which contains the nucleic acids) and an organic phase (which contains other cellular components, including proteins). Commonly used protocols require the use of salts in conjunction with phenol (P. Chomczynski and N. Sacchi, Anal. Biochem. 162:156 [1987]), or employ a centrifugation step to remove the protein (R. J. Slater, supra).

Once the nucleic acid fraction has been isolated from the cell, the structure of the mRNA molecule may be used to assist in the purification of mRNA from DNA and other RNA molecules. Because the mRNA of higher organisms is usually polyadenylated on its 3' end ("poly-A tail" or "poly-A track"), one means of isolating RNA from cells has been based on binding the poly-A tail with its complementary sequence (i.e., oligo-dT), that has been linked to a support such as cellulose. Commonly, the hybridized mRNA/oligo-dT is separated from the other components present in the sample through centrifugation or, in the case of magnetic formats, exposure to a magnetic field. Once the hybridized mRNA/oligo-dT is separated from the other sample components, the mRNA is usually removed from the oligo-dT. However, for some applications, the mRNA may remain bound to the oligo-dT that is linked to a solid support.

A wide variety of solid supports with linked oligo-dT have been developed and are commercially available. Cellulose remains the most common support for most oligo-dT systems, although formats with oligo-dT covalently linked to latex beads and paramagnetic particles have also been developed and are commercially available. The paramagnetic particles may be used in a biotin-avidin system, in which biotinylated oligo-dT is annealed in solution to mRNA. The hybrids are then captured with streptavidin-coated paramagnetic particles, and separated using a magnetic field. In addition to these methods, variations exist, such as affinity purification of polyadenylated RNA from eukaryotic total RNA in a spun-column format. These approaches allow for hybridization of poly-A mRNA, but vary in efficiency and sensitivity.

In one embodiment, the mRNA is treated with reverse transcriptase to make cDNA. The cDNA can be used in primer extension and PCR using the primers described below. Thus, the present invention contemplates nucleic acid molecules detectable by primer extension suing the primers described below. Primer extension (and PCR for that matter) can be carried out under conditions (so-called "high stringency conditions") such that only complementary nucleic acid will hybridize (as opposed to hybridization with partially complementary nucleic acid). These conditions including annealing at or near the melting temperature of the duplex.

Primers Directed To A Specific Disintegrin Metalloprotease Gene

The invention provides a partial nucleic acid full length protein coding region sequence of a novel disintegrin metalloprotease gene useful for, among other things, the detection of disintegrin metalloprotease gene expression. In one embodiment, primers directed to a portion of this partial sequence are use to detect the presence or absence of the gene sequence. These primers can be also be used for the identification of a cDNA clone representing the entire gene, allowing for recombinant expression in a host cell of the nucleic acid sequence encoding the disintegrin metalloprotease or fragments (or mutants) thereof.

Preferred primers are primer SEQ ID NO:9 (5'-AGCCTGTGTC-3') and SEQ ID NO:10 (5'-AGCCTGTGTCTGAACCACT-3'). However, other primers can be readily designed from the sequences set forth in SEQ ID NO:5 and SEQ ID NO:1.

Method of Comparing Biological Samples by Differential Display

Successful amplification can be confirmed by characterization of the product(s) from the reaction. It is not intended that the present invention be limited by the method by which extension products or PCR products are detected. In one embodiment, the PCR products are analyzed by high resolution agarose gel electrophoresis using 2% agarose gels (BRL) and the amplified DNA fragments are visualized by ethidium bromide staining and UV transillumination. The present invention contemplates, in one embodiment, using electrophoresis to confirm product formation and compare the results between samples.

Hence, the present invention contemplates detection of sequences of the novel disintegrin metalloprotease gene in mixtures of nucleic acid (e.g., cDNA or RT-mRNA). By carrying out PCR on a mixture of nucleic acid and running the products on gels, nucleic acid comprising a sequence that is defined by the primers is "isolated." The product can thereafter be "purified" by cutting the band from the gel (or by other suitable methods such as electroelution).

Synopsis of the Sequence Listing

For the aid of the reader, the inter-relation of the sequence listings are described hereinbelow:

SEQ ID NO:1 is a fragmentary DNA sequence, and is part of SEQ ID NO:3. The first base (Cytosine or C) of SEQ ID NO:1 is base 940 of SEQ ID NO:3. The DNA sequences are identical where they overlap.

SEQ ID NO:2 and SEQ ID NO:4, are the expressed amino acid sequences of SEQ ID NO:1 and SEQ ID NO:3 respectively. The first amino acid of SEQ ID NO:2, Gln, is the 309th amino acid in SEQ ID NO:4. The two sequences are homologous to the carboxy terminus of the protein.

SEQ ID NO:7 is a sense strand of DNA provided by differential display experiments. The first base of SEQ ID NO:7 corresponds to base 1371 of SEQ ID NO:1, and to base 2310 of SEQ ID NO:3. These sequences are homologous for 452 bases, to base 1822 of SEQ ID NO:1 and to base 2761 of SEQ ID NO:3. The difference in the last two bases of SEQ ID NO:1 and SEQ ID NO:3 may be due to errors in sequencing or a common replicatory error found in PCR, or may be part of a cloning vector. SEQ ID NO:7 continues some 284 bases beyond the homology, and thus well beyond the terminus of SEQ ID NO:1 and SEQ ID NO:3.

In addition, bases 477 to 716 of SEQ ID NO:7 are the SEQ ID NO 6. SEQ ID NO 6 is the sense strand of SEQ ID NO:5, which is an antisense strand found via differential display cloning. Hence SEQ ID NO:6 shows the DNA orientation as it would appear in the mRNA. These two sequences are found near the 3' end of this gene.

Although bases 452 to the 3' end of SEQ ID NO:7 differ from SEQ ID NO:1 and SEQ ID NO:3, SEQ ID NO:7 is nonetheless valid. It is essential to note that the expressed peptide sequence is not affected by this difference. It is likely these bases do not appear in SEQ ID NO:1 and SEQ ID NO:3 because of the use of an alternative polyadenylation signal.

SEQ ID NO 8 is a novel full length DNA sequence. SEQ ID NO:9 is the novel expressed protein of SEQ ID NO:8. SEQ ID NO:9 differs from SEQ ID NO:4 in that amino acids 162 (Ser)-213 (Tyr) of SEQ ID NO:4 is replaced by a single residue, Asn, at position 162 of SEQ ID NO:9. That change is reflected in the DNA by a deletion bases 501–654 for a total of 153 bases, leaving the reading frame intact but changing one residue and deleting the 51 amino acids present in SEQ ID NO:4.

SEQ ID NO:10 and SEQ ID NO:11 are antisense primers useful in PCR, and are the inverse of the 3' terminus of SEQ ID NO:7, other sequences for primers are discernible by the skilled artisan using sequences referred to herein.

EXAMPLES

The following non-limiting examples illustrate a preferred embodiment of the present invention, and briefly describe the uses of the present invention. These examples are provided for the guidance of the skilled artisan, and do not limit the invention in any way. Armed with this disclosure and these examples the skilled artisan is capable of making and using the claimed invention.

Standard starting materials are used for these examples. Many of these materials are known and commercially available. For example, *E. coli* CJ236 and JM101 are known strains, pUB110 is a known plasmid and Kunkel method mutagenesis is also well known in the art. In addition certain cell lines and cDNA may be commercially available, for example U-937, available from Clontech Inc., Palo Alto, Calif.

Variants may be made by expression systems and by various methods in various hosts, these methods are within the scope of the practice of the skilled artisan in molecular biology, biochemistry or other arts related to biotechnology.

Example 1

RNA is isolated from unstimulated and interleukin-1 stimulated cultures of normal human articular chondrocytes. The RNA is reverse transcribed into cDNA. The cDNA is subjected to a modified differential display procedure using a series of random primers.

PCR samples generated from both stimulated and unstimulated chondrocytes are electrophoresed in adjacent lanes on polyacrylamide gels. The differentially expressed band is excised from the gel, cloned, and sequenced. The differential expression of the gene is confirmed by RNAase protection and nuclear run on experiments.

Example 2

A novel partial human cDNA coding the protein is cloned from primary cultures of interleukin-1 stimulated human articular (femoral head) chondrocytes, using known methods. The same sequence is found, and the gene completed by screening of human cDNA libraries to obtain full length clones.

Example 3

The cloned DNA of example 2 is placed in pUB110 using known methods.

This plasmid is used to transform *E. coli* and provides a template for site-directed mutagenesis to create new mutants. Kunkel method mutagenesis was performed altering the Gln 1 to Ala.

Example 4

[$^{125}$I] disintegrin antibody is prepared using IODO-BEADS (Pierce, Rockford, Ill.; immobilized chloramine-T on nonporous polystyrene beads). Lyophilized antibody (2 $\mu$g) is taken up in 50 $\mu$l of 10 mM acetic acid and added to 450 $\mu$l of phosphate-buffered saline (PBS) (Sigma, St. Louis, Mo.) on ice. To the tube is added 500 $\mu$Curie of $^{125}$I (Amersham, Arlington Heights, Ill.) (2200 Ci/mmol) in 5 $\mu$l, and one IODOBEAD. The reaction is incubated on ice for 10 min with occasional shaking. The reaction is then terminated by removal of the reaction from the IODOBEAD. To remove unreacted $^{125}$I, the mixture is applied to a PD-10 gel filtration column.

Example 5

A fluorogenic disintegrin metalloprotease substrate peptide (Bachem, Guelph Mills, King of Prussia, Pa.) is mixed with the disintegrin and change in the fluorescence is evaluated at 2 min, as a control. Then the fluorogenic peptide is mixed with the disintegrin in the presence of the compound (metalloprotease inhibitor) in evaluation in a separate run, with evaluation at various time points over 2 to 12 hours. Data are evaluated using standard methodology to provide relative binding of the evaluated compound.

Example 6

0.5 ml of synovial fluid from the left knee of a patient is withdrawn and tested for elevated levels disintegrin by ELISA. The results indicate higher than normal disintegrin level. The patient is prescribed a prophylactic dose of a disintegrin inhibitor administered orally over time or is administered an injection of same in the left knee before leaving the clinician's office.

Example 7

Inhibition of extracellular matrix remodeling is explored via inhibition of disintegrin metalloprotease activity. Using a small molecular weight, synthetic metalloprotease inhibitor, such as those used to inhibit the matrix metalloproteases, tissue integrity and proteoglycan is monitored.

A sample of IL-I stimulated bovine nasal cartilage derived articular cartilage is grown in a 1 micromolar solution of a small molecular weight disintegrin inhibitor. The experiment is controlled and compared to an identical culture grown with no inhibitor.

The assay of the culture after 7 days shows that the inhibited culture has less tissue breakdown and less proteoglycan present in the serum of the culture. The result is consistent with the inhibited aggrecanase activity. Inhibition of aggrecanase would inhibit tissue breakdown and reduce the release of proteoglycan.

Example 8

Inhibition of proteolytic processing resulting in the release from the membrane bound form of the disintegrin metalloprotease domain inhibits "second messenger" signaling of the membrane bound disintegrin molecule. Such second messenger signaling would result in cellular phenotypic changes, changes in gene expression, changes in mitotic activity, and the like.

Cells known to contain disintegrin are treated with a serine protease. Proteins released from the cell are measured by standard methods. Specifically the metalloprotease activity is monitored via literature methods. The amount of metalloprotease released is correlated to the amount of serine protease used to treat the cells.

Increases, versus control, in src tyrosine kinase activity are measured by Western blot analysis of intracellular proteins using monoclonal antibodies specific for phosphotyrosine following cleavage and release of the disintegrin metalloprotease. Controls are cells that have not been treated with serine protease.

src tyrosine kinase activity in the cell (or is it cell culture) is measured by literature methods. Release of the metalloprotease domain of the disintegrin is also monitored via literature methods. There is a direct correlation between release of the metalloprotease domain and increases in intracellular src tyrosine kinase activity. This result is consistent with stimulation of disintegrin-mediated cell signaling by stimulation of the src tyrosine kinase cascade.

Example 9

Integrin binding is measured with a peptide containing the sequence RGD. Inhibition of intercellular adhesion molecules, or extracellular matrix components results in the inhibition of phenotypic changes, including changes in cell shape, associated with such interactions. Integrin binding is measured via competitive assay, using cellular changes in shape visible via microscopy. The peptide inhibits such cellular changes.

This result is consistent with competition with or blocking of the interaction of disintegrin. The RGD peptide inhibits cellular changes in chondrocytes. The osteoarthritis phenotype, characterized by increased matrix synthesis and accelerated matrix metalloprotease activity does not occur. Other readily assayable cellular changes can be used to monitor this result, including gene expression, changes in mitotic activity, and the like.

Example 10

A small molecular weight metalloprotease inhibitor is used to treat a tissue culture according to the method of Example 7. The release of TNF-α from the cell membrane is measured by literature methods. The inhibitor of Example 7 also decreases the amount of TNF-α secreted from the cell membrane.

Hence it is contemplated that inhibition of disintegrin metalloprotease activity will result in the inhibition of a disintegrin associated inflammation cascade and secretase activity. It is contemplated that monitoring the release of cytokines or IL-1 from the cell membrane, and the like, will produce the same result.

Example 11

Differential Display Screening for Disease

RNA is isolated from unstimulated and interleukin-1 stimulated cultures of normal human articular chondrocytes. The RNA is reverse transcribed into cDNA. The cDNA is subjected to amplification (PCR) using the above-named primers. PCR samples generated from both stimulated and unstimulated chondrocytes are electrophoresed in adjacent lanes on polyacrylamide gels. A differentially expressed band (i.e., a band found only in the stimulated cells and not expressed at significant or detectable levels in the unstimulated cells) is excised from the gel, cloned, and partially sequenced. The partial sequence is shown in SEQ ID NO:5. the sequence is found to exhibit approximately 60% homology to a rat metalloprotease (see above). The sequence is found to exhibit approximately 85% homology to a human metalloprotease (see Gen Bank Accession #Z48579, see FIG. 2).

Example 12

Screening for Metastatic Potential of Tumors

Cancer tissue is tested for metalloprotease gene expression. The above-named primers are used in PCR on extracted nucleic acid from the sample. High levels of transcripts suggest metastatic potential.

Example 13

Drug Screen for Expression Inhibitors

Candidate inhibitors of metalloprotease gene expression are screened in vitro. Interleukin-1 stimulated cultures of normal human articular chondrocytes are exposed in vitro to candidate inhibitors. The RNA is isolated and reverse transcribed into cDNA. the cDNA is subjected to amplification (PCR) using the above-named primers. PCR samples generated from both chondrocytes exposed to inhibitors and uninhibited chondrocytes are electrophoreses in adjacent lanes on polyacrylamide gels. Reduced levels of PCR product identifies an inhibitor.

Example 14

Drug Screen For Metalloprotease Inhibitors

Candidate inhibitors of the metalloprotease itself are screened in vitro. The culture supernatant of Interleukin-1 stimulated cultures of normal human articular chondrocytes are assayed on suitable metalloprotease substrates (e.g., matrix proteins) in the presence and absence of candidate inhibitors. Known inhibitors are used as controls (e.g., 1,10-phenanthroline available commercially from Sigma Co., St. Louis). Reduced levels of substrate (e.g., fluorogenic disintegrin metalloprotease substrate) degradation identifies an inhibitor.

Example 15

A 1400 BP clone is isolated via standard screening techniques from U-937, a monocyte-like cell cDNA line library. The initial sequence is a truncated clone, missing a portion of the 5' end. The 5' end is generated using 5' R.A.C.E. (Rapid Amplification of 5 c-DNA Ends, see for example, Chapter 4 (pages 28–38), and references therein of *PCR Protocols, A Guide to Methods and Applications*, Innis, et al, eds. 1990 Academic Press), a known technique, generating a 1600 bp clone containing the remaining 5' sequence. These two sequences together provide SEQ ID NO:8, from which the peptide sequence is derived.

Example 16

Primers SEQ ID NO:9 (5'-AGCCTGTGTC-3') and SEQ ID NO:10 (5'-AGCCTGTGTCTGAACCACT-3') are used in differential display of mRNA (ddrt-PCR). 2–5 ng of sscDNA is used in the PCR. The reaction is set up in precooled 0.2 µl thin-walled tubes on ice. Each tube containing, 50 mM TrisHCl (pH 8.5), 50 mM KCl, 1.5 mM $MgCl_2$ 1 mM of each dNTP, 2–5 ng of sscDNA, 10 pmoles of each primer above, 05. µl of α-$p^{33}$ dCTP (10 µCi/µl, Amersham) and water to 20 µl. The mixture is subjected to 35 cycles of denaturation (94° C. for 30 sec.), annealing (36° C. for 30 sec.) and extension (72° C. for 1 min.) using a Perkin-Elmer System 2400 Thermal Cycler (Perking-Elmer, Norwalk, Conn.).

By this method, IL-1 treated chondrocytes expressed the mRNA associated with this gene, while the untreated (no IL-1) control chondrocytes expressed no detectable mRNA.

Example 17

Assay system amenable to high throughout screening

The protease activity of disintegrin is measured in a kinetic enzyme inhibition assay using a fluorescent substrate. Using cloned disintegrin enzyme, and a small MW fluorescently labeled protein as the substrate. Enzyme activity is quantified by measurement of fluorescence after cleavage of the substrate molecule at room temperature. This assay simple and very easy to automate.

Using standard techniques, this assay is adapted to 96 or 384 well plates.

All references described herein are hereby incorporated by reference.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. An isolated human disintegrin, comprising the amino acid sequence as set forth in SEQ ID NO:9.

2. A screening kit for identifying compounds that inhibit the disintegrin of claim 1 comprising the purified disintegrin of claim 1.

3. A method for identifying compounds that inhibit the disintegrin of claim 1, comprising:

a. providing the disintegrin of claim 1;
b. contacting the disintegrin with a candidate inhibitor;
c. determining the level of disintegrin activity in the presence of the candidate inhibitor, wherein a decrease in the activity is an indication that the candidate inhibitor inhibits the activity of the disintegrin.

* * * * *

SEQUENCE LISTING

<160> NUMBER OF SEQ ID NOS: 11

<210> SEQ ID NO 1
<211> LENGTH: 1824
<212> TYPE: DNA
<213> ORGANISM: Homo sapiens
<220> FEATURE:
<221> NAME/KEY: CDS
<222> LOCATION: (2)..(1474)

<400> SEQUENCE: 1

```
c cag acc aca gac ttc tcc gga atc cgt aac atc agt ttc atg gtg aaa        49
  Gln Thr Thr Asp Phe Ser Gly Ile Arg Asn Ile Ser Phe Met Val Lys
    1               5                  10                  15 cgc ata aga atc aat aca act gct gat gag aag gac cct aca aat cct          97
Arg Ile Arg Ile Asn Thr Thr Ala Asp Glu Lys Asp Pro Thr Asn Pro
                 20                  25                  30 ttc cgt ttc cca aat att agt gtg gag aag ttt ctg gaa ttg aat tct         145
Phe Arg Phe Pro Asn Ile Ser Val Glu Lys Phe Leu Glu Leu Asn Ser
         35                  40                  45 gag cag aat cat gat gac tac tgt ttg gcc tat gtc ttc aca gac cga         193
Glu Gln Asn His Asp Asp Tyr Cys Leu Ala Tyr Val Phe Thr Asp Arg
 50                  55                  60 gat ttt gat gat ggc gta ctt ggt ctg gct tgg gtt gga gca cct tca         241
Asp Phe Asp Asp Gly Val Leu Gly Leu Ala Trp Val Gly Ala Pro Ser
 65                  70                  75                  80 gga agc tct gga gga ata tgt gaa aaa agt aaa ctc tat tca gat ggt         289
Gly Ser Ser Gly Gly Ile Cys Glu Lys Ser Lys Leu Tyr Ser Asp Gly
                 85                  90                  95 aag aag aag tcc tta aac act gga att att act gtt cag aac tat ggg         337
Lys Lys Lys Ser Leu Asn Thr Gly Ile Ile Thr Val Gln Asn Tyr Gly
            100                 105                 110 tct cat gta cct ccc aaa gtc tct cac att act ttt gct cac gaa gtt         385
Ser His Val Pro Pro Lys Val Ser His Ile Thr Phe Ala His Glu Val
        115                 120                 125 gga cat aac ttt gga tcc cca cat gat tct gga aca gag tgc aca cca         433
Gly His Asn Phe Gly Ser Pro His Asp Ser Gly Thr Glu Cys Thr Pro
    130                 135                 140 gga gaa tct aag aat ttg ggt caa aaa gaa aat ggc aat tac atc atg         481
Gly Glu Ser Lys Asn Leu Gly Gln Lys Glu Asn Gly Asn Tyr Ile Met
145                 150                 155                 160 tat gca aga gca aca tct ggg gac aaa ctt aac aac aat aaa ttc tca         529
Tyr Ala Arg Ala Thr Ser Gly Asp Lys Leu Asn Asn Asn Lys Phe Ser
                165                 170                 175 ctc tgt agt att aga aat ata agc caa gtt ctt gag aag aag aga aac         577
Leu Cys Ser Ile Arg Asn Ile Ser Gln Val Leu Glu Lys Lys Arg Asn
            180                 185                 190 aac tgt ttt gtt gaa tct ggc caa cct att tgt gga aat gga atg gta         625
Asn Cys Phe Val Glu Ser Gly Gln Pro Ile Cys Gly Asn Gly Met Val
        195                 200                 205 gaa caa ggt gaa gaa tgt gat tgt ggc tat agt gac cag tgt aaa gat         673
Glu Gln Gly Glu Glu Cys Asp Cys Gly Tyr Ser Asp Gln Cys Lys Asp
    210                 215                 220 gaa tgc tgc ttc gat gca aat caa cca gag gga aga aaa tgc aaa ctg         721
Glu Cys Cys Phe Asp Ala Asn Gln Pro Glu Gly Arg Lys Cys Lys Leu
225                 230                 235                 240 aaa cct ggg aaa cag tgc agt cca agt caa ggt cct tgt tgt aca gca         769
Lys Pro Gly Lys Gln Cys Ser Pro Ser Gln Gly Pro Cys Cys Thr Ala
                245                 250                 255
```

```
cag tgt gca ttc aag tca aag tct gag aag tgt cgg gat gat tca gac      817
Gln Cys Ala Phe Lys Ser Lys Ser Glu Lys Cys Arg Asp Asp Ser Asp
            260                 265                 270 tgt gca agg gaa gga ata tgt aat ggc ttc aca gct ctc tgc cca gca      865
Cys Ala Arg Glu Gly Ile Cys Asn Gly Phe Thr Ala Leu Cys Pro Ala
275                 280                 285 tct gac cct aaa cca aac ttc aca gac tgt aat agg cat aca caa gtg      913
Ser Asp Pro Lys Pro Asn Phe Thr Asp Cys Asn Arg His Thr Gln Val
        290                 295                 300 tgc att aat ggg caa tgt gca ggt tct atc tgt gag aaa tat ggc tta      961
Cys Ile Asn Gly Gln Cys Ala Gly Ser Ile Cys Glu Lys Tyr Gly Leu
305                 310                 315                 320 gag gag tgt acg tgt gcc agt tct gat ggc aaa gat gat aaa gaa tta      1009
Glu Glu Cys Thr Cys Ala Ser Ser Asp Gly Lys Asp Asp Lys Glu Leu
                325                 330                 335 tgc cat gta tgc tgt atg aag aaa atg gac cca tca act tgt gcc agt      1057
Cys His Val Cys Cys Met Lys Lys Met Asp Pro Ser Thr Cys Ala Ser
            340                 345                 350 aca ggg tct gtg cag tgg agt agg cac ttc agt ggt cga acc atc acc      1105
Thr Gly Ser Val Gln Trp Ser Arg His Phe Ser Gly Arg Thr Ile Thr
        355                 360                 365 ctg caa cct gga tcc cct tgc aac gat ttt aga ggt tac tgt gat gtt      1153
Leu Gln Pro Gly Ser Pro Cys Asn Asp Phe Arg Gly Tyr Cys Asp Val
370                 375                 380 ttc atg cgg tgc aga tta gta gat gct gat ggt cct cta gct agg ctt      1201
Phe Met Arg Cys Arg Leu Val Asp Ala Asp Gly Pro Leu Ala Arg Leu
385                 390                 395                 400 aaa aaa gca att ttt agt cca gag ctc tat gaa aac att gct gaa tgg      1249
Lys Lys Ala Ile Phe Ser Pro Glu Leu Tyr Glu Asn Ile Ala Glu Trp
                405                 410                 415 att gtg gct cat tgg tgg gca gta tta ctt atg gga att gct ctg atc      1297
Ile Val Ala His Trp Trp Ala Val Leu Leu Met Gly Ile Ala Leu Ile
            420                 425                 430 atg cta atg gct gga ttt att aag ata tgc agt gtt cat act cca agt      1345
Met Leu Met Ala Gly Phe Ile Lys Ile Cys Ser Val His Thr Pro Ser
        435                 440                 445 agt aat cca aag ttg cct cct cct aaa cca ctt cca ggc act tta aag      1393
Ser Asn Pro Lys Leu Pro Pro Pro Lys Pro Leu Pro Gly Thr Leu Lys
450                 455                 460 agg agg aga cct cca cag ccc att cag caa ccc cag cgt cag cgg ccc      1441
Arg Arg Arg Pro Pro Gln Pro Ile Gln Gln Pro Gln Arg Gln Arg Pro
465                 470                 475                 480 cga gag agt tat caa atg gga cac atg aga cgc taactgcagc ttttgccttg   1494
Arg Glu Ser Tyr Gln Met Gly His Met Arg Arg
                485                 490 gttcttccta gtgcctacaa tgggaaaact tcactccaaa gagaaaccta ttaagtcatc   1554
atctccaaac taaaccctca caagtaacag ttgaagaaaa aatggcaaga gatcatatcc   1614
tcagaccagg tggaattact taaattttaa agcctgaaaa ttccaatttg ggggtgggag   1674
gtggaaaagg aacccaattt tcttatgaac agatattttt aacttaatgg cacaaagtct   1734
tagaatatta ttatgtgccc cgtgttccct gttcttcgtt gctgcatttt cttcacttgc   1794
aggcaaactt ggctctcaat aaactttcg                                     1824

<210> SEQ ID NO 2
<211> LENGTH: 491
<212> TYPE: PRT
<213> ORGANISM: Homo sapiens
```

-continued

```
<400> SEQUENCE: 2

Gln Thr Thr Asp Phe Ser Gly Ile Arg Asn Ile Ser Phe Met Val Lys
 1               5                  10                  15

Arg Ile Arg Ile Asn Thr Thr Ala Asp Glu Lys Asp Pro Thr Asn Pro
             20                  25                  30

Phe Arg Phe Pro Asn Ile Ser Val Glu Lys Phe Leu Glu Leu Asn Ser
         35                  40                  45

Glu Gln Asn His Asp Asp Tyr Cys Leu Ala Tyr Val Phe Thr Asp Arg
     50                  55                  60

Asp Phe Asp Asp Gly Val Leu Gly Leu Ala Trp Val Gly Ala Pro Ser
 65                  70                  75                  80

Gly Ser Ser Gly Gly Ile Cys Glu Lys Ser Lys Leu Tyr Ser Asp Gly
                 85                  90                  95

Lys Lys Lys Ser Leu Asn Thr Gly Ile Ile Thr Val Gln Asn Tyr Gly
             100                 105                 110

Ser His Val Pro Pro Lys Val Ser His Ile Thr Phe Ala His Glu Val
         115                 120                 125

Gly His Asn Phe Gly Ser Pro His Asp Ser Gly Thr Glu Cys Thr Pro
     130                 135                 140

Gly Glu Ser Lys Asn Leu Gly Gln Lys Glu Asn Gly Asn Tyr Ile Met
145                 150                 155                 160

Tyr Ala Arg Ala Thr Ser Gly Asp Lys Leu Asn Asn Asn Lys Phe Ser
                165                 170                 175

Leu Cys Ser Ile Arg Asn Ile Ser Gln Val Leu Glu Lys Lys Arg Asn
            180                 185                 190

Asn Cys Phe Val Glu Ser Gly Gln Pro Ile Cys Gly Asn Gly Met Val
        195                 200                 205

Glu Gln Gly Glu Glu Cys Asp Cys Gly Tyr Ser Asp Gln Cys Lys Asp
    210                 215                 220

Glu Cys Cys Phe Asp Ala Asn Gln Pro Glu Gly Arg Lys Cys Lys Leu
225                 230                 235                 240

Lys Pro Gly Lys Gln Cys Ser Pro Ser Gln Gly Pro Cys Cys Thr Ala
                245                 250                 255

Gln Cys Ala Phe Lys Ser Lys Ser Glu Lys Cys Arg Asp Asp Ser Asp
            260                 265                 270

Cys Ala Arg Glu Gly Ile Cys Asn Gly Phe Thr Ala Leu Cys Pro Ala
        275                 280                 285

Ser Asp Pro Lys Pro Asn Phe Thr Asp Cys Asn Arg His Thr Gln Val
    290                 295                 300

Cys Ile Asn Gly Gln Cys Ala Gly Ser Ile Cys Glu Lys Tyr Gly Leu
305                 310                 315                 320

Glu Glu Cys Thr Cys Ala Ser Ser Asp Gly Lys Asp Lys Glu Leu
                325                 330                 335

Cys His Val Cys Cys Met Lys Lys Met Asp Pro Ser Thr Cys Ala Ser
            340                 345                 350

Thr Gly Ser Val Gln Trp Ser Arg His Phe Ser Gly Arg Thr Ile Thr
        355                 360                 365

Leu Gln Pro Gly Ser Pro Cys Asn Asp Phe Arg Gly Tyr Cys Asp Val
    370                 375                 380

Phe Met Arg Cys Arg Leu Val Asp Ala Asp Gly Pro Leu Ala Arg Leu
385                 390                 395                 400

Lys Lys Ala Ile Phe Ser Pro Glu Leu Tyr Glu Asn Ile Ala Glu Trp
                405                 410                 415
```

-continued

```
Ile Val Ala His Trp Trp Ala Val Leu Leu Met Gly Ile Ala Leu Ile
            420                 425                 430
Met Leu Met Ala Gly Phe Ile Lys Ile Cys Ser Val His Thr Pro Ser
        435                 440                 445
Ser Asn Pro Lys Leu Pro Pro Lys Pro Leu Pro Gly Thr Leu Lys
    450                 455                 460
Arg Arg Arg Pro Gln Pro Ile Gln Gln Pro Gln Arg Gln Arg Pro
465                 470                 475                 480
Arg Glu Ser Tyr Gln Met Gly His Met Arg Arg
                485                 490

<210> SEQ ID NO 3
<211> LENGTH: 2763
<212> TYPE: DNA
<213> ORGANISM: Homo sapiens
<220> FEATURE:
<221> NAME/KEY: CDS
<222> LOCATION: (17)..(2413)

<400> SEQUENCE: 3
ggcggcggca cggaag atg gtg ttg ctg aga gtg tta att ctg ctc ctc tcc       52
                  Met Val Leu Leu Arg Val Leu Ile Leu Leu Leu Ser
                    1               5                  10 tgg gcg gcg ggg atg gga ggt cag tat ggg aat cct tta aat aaa tat       100
Trp Ala Ala Gly Met Gly Gly Gln Tyr Gly Asn Pro Leu Asn Lys Tyr
            15                  20                  25 atc aga cat tat gaa gga tta tct tac aat gtg gat tca tta cac caa       148
Ile Arg His Tyr Glu Gly Leu Ser Tyr Asn Val Asp Ser Leu His Gln
    30                  35                  40 aaa cac cag cgt gcc aaa aga gca gtc tca cat gaa gac caa ttt tta       196
Lys His Gln Arg Ala Lys Arg Ala Val Ser His Glu Asp Gln Phe Leu
45                  50                  55                  60 cgt cta gat ttc cat gcc cat gga aga cat ttc aac cta cga atg aag       244
Arg Leu Asp Phe His Ala His Gly Arg His Phe Asn Leu Arg Met Lys
                65                  70                  75 agg gac act tcc ctt ttc agt gat gaa ttt aaa gta gaa aca tca aat       292
Arg Asp Thr Ser Leu Phe Ser Asp Glu Phe Lys Val Glu Thr Ser Asn
        80                  85                  90 aaa gta ctt gat tat gat acc tct cat att tac act gga cat att tat       340
Lys Val Leu Asp Tyr Asp Thr Ser His Ile Tyr Thr Gly His Ile Tyr
    95                  100                 105 ggt gaa gaa gga agt ttt agc cat ggg tct gtt att gat gga aga ttt       388
Gly Glu Glu Gly Ser Phe Ser His Gly Ser Val Ile Asp Gly Arg Phe
110                 115                 120 gaa gga ttc atc cag act cgt ggt ggc aca ttt tat gtt gag cca gca       436
Glu Gly Phe Ile Gln Thr Arg Gly Gly Thr Phe Tyr Val Glu Pro Ala
125                 130                 135                 140 gag aga tat att aaa gac cga act ctg cca ttt cac tct gtc att tat       484
Glu Arg Tyr Ile Lys Asp Arg Thr Leu Pro Phe His Ser Val Ile Tyr
                145                 150                 155 cat gaa gat gat att agt gaa agg ctt aaa ctg agg ctt aga aaa ctt       532
His Glu Asp Asp Ile Ser Glu Arg Leu Lys Leu Arg Leu Arg Lys Leu
        160                 165                 170 atg tca ctt gag ttg tgg acc tcc tgt tgt tta ccc tgt gct ctt ctg       580
Met Ser Leu Glu Leu Trp Thr Ser Cys Cys Leu Pro Cys Ala Leu Leu
    175                 180                 185 ctt cac tca tgg aag aaa gct gta aat tct cac tgc ctt tac ttc aag       628
Leu His Ser Trp Lys Lys Ala Val Asn Ser His Cys Leu Tyr Phe Lys
190                 195                 200
```

```
                                                     -continued gat ttc tgg ggc ttt tct gaa atc tac tat ccc cat aaa tac ggt cct      676
Asp Phe Trp Gly Phe Ser Glu Ile Tyr Tyr Pro His Lys Tyr Gly Pro
205             210                 215                 220 cag ggc ggc tgt gca gat cat tca gta ttt gaa aga atg agg aaa tac      724
Gln Gly Gly Cys Ala Asp His Ser Val Phe Glu Arg Met Arg Lys Tyr
                    225                 230                 235 cag atg act ggt gta gag gaa gta aca cag ata cct caa gaa gaa cat      772
Gln Met Thr Gly Val Glu Glu Val Thr Gln Ile Pro Gln Glu Glu His
            240                 245                 250 gct gct aat ggt cca gaa ctt ctg agg aaa aga cgt aca act tca gct      820
Ala Ala Asn Gly Pro Glu Leu Leu Arg Lys Arg Arg Thr Thr Ser Ala
        255                 260                 265 gaa aaa aat act tgt cag ctt tat att cag act gat cat ttg ttc ttt      868
Glu Lys Asn Thr Cys Gln Leu Tyr Ile Gln Thr Asp His Leu Phe Phe
270                 275                 280 aaa tat tac gga aca cga gaa gct gtg att gcc cag ata tcc agt cat      916
Lys Tyr Tyr Gly Thr Arg Glu Ala Val Ile Ala Gln Ile Ser Ser His
285                 290                 295                 300 gtt aaa gcg att gat aca att tac cag acc aca gac ttc tcc gga atc      964
Val Lys Ala Ile Asp Thr Ile Tyr Gln Thr Thr Asp Phe Ser Gly Ile
                    305                 310                 315 cgt aac atc agt ttc atg gtg aaa cgc ata aga atc aat aca act gct     1012
Arg Asn Ile Ser Phe Met Val Lys Arg Ile Arg Ile Asn Thr Thr Ala
                320                 325                 330 gat gag aag gac cct aca aat cct ttc cgt ttc cca aat att agt gtg     1060
Asp Glu Lys Asp Pro Thr Asn Pro Phe Arg Phe Pro Asn Ile Ser Val
            335                 340                 345 gag aag ttt ctg gaa ttg aat tct gag cag aat cat gat gac tac tgt     1108
Glu Lys Phe Leu Glu Leu Asn Ser Glu Gln Asn His Asp Asp Tyr Cys
        350                 355                 360 ttg gcc tat gtc ttc aca gac cga gat ttt gat gat ggc gta ctt ggt     1156
Leu Ala Tyr Val Phe Thr Asp Arg Asp Phe Asp Asp Gly Val Leu Gly
365                 370                 375                 380 ctg gct tgg gtt gga gca cct tca gga agc tct gga gga ata tgt gaa     1204
Leu Ala Trp Val Gly Ala Pro Ser Gly Ser Ser Gly Gly Ile Cys Glu
                    385                 390                 395 aaa agt aaa ctc tat tca gat ggt aag aag aag tcc tta aac act gga     1252
Lys Ser Lys Leu Tyr Ser Asp Gly Lys Lys Lys Ser Leu Asn Thr Gly
                400                 405                 410 att att act gtt cag aac tat ggg tct cat gta cct ccc aaa gtc tct     1300
Ile Ile Thr Val Gln Asn Tyr Gly Ser His Val Pro Pro Lys Val Ser
            415                 420                 425 cac att act ttt gct cac gaa gtt gga cat aac ttt gga tcc cca cat     1348
His Ile Thr Phe Ala His Glu Val Gly His Asn Phe Gly Ser Pro His
        430                 435                 440 gat tct gga aca gag tgc aca cca gga gaa tct aag aat ttg ggt caa     1396
Asp Ser Gly Thr Glu Cys Thr Pro Gly Glu Ser Lys Asn Leu Gly Gln
445                 450                 455                 460 aaa gaa aat ggc aat tac atc atg tat gca aga gca aca tct ggg gac     1444
Lys Glu Asn Gly Asn Tyr Ile Met Tyr Ala Arg Ala Thr Ser Gly Asp
                    465                 470                 475 aaa ctt aac aac aat aaa ttc tca ctc tgt agt att aga aat ata agc     1492
Lys Leu Asn Asn Asn Lys Phe Ser Leu Cys Ser Ile Arg Asn Ile Ser
                480                 485                 490 caa gtt ctt gag aag aag aga aac aac tgt ttt gtt gaa tct ggc caa     1540
Gln Val Leu Glu Lys Lys Arg Asn Asn Cys Phe Val Glu Ser Gly Gln
            495                 500                 505 cct att tgt gga aat gga atg gta gaa caa ggt gaa gaa tgt gat tgt     1588
Pro Ile Cys Gly Asn Gly Met Val Glu Gln Gly Glu Glu Cys Asp Cys
        510                 515                 520
```

```
ggc tat agt gac cag tgt aaa gat gaa tgc tgc ttc gat gca aat caa       1636
Gly Tyr Ser Asp Gln Cys Lys Asp Glu Cys Cys Phe Asp Ala Asn Gln
525                 530                 535                 540 cca gag gga aga aaa tgc aaa ctg aaa cct ggg aaa cag tgc agt cca       1684
Pro Glu Gly Arg Lys Cys Lys Leu Lys Pro Gly Lys Gln Cys Ser Pro
                545                 550                 555 agt caa ggt cct tgt tgt aca gca cag tgt gca ttc aag tca aag tct       1732
Ser Gln Gly Pro Cys Cys Thr Ala Gln Cys Ala Phe Lys Ser Lys Ser
            560                 565                 570 gag aag tgt cgg gat gat tca gac tgt gca agg gaa gga ata tgt aat       1780
Glu Lys Cys Arg Asp Asp Ser Asp Cys Ala Arg Glu Gly Ile Cys Asn
        575                 580                 585 ggc ttc aca gct ctc tgc cca gca tct gac cct aaa cca aac ttc aca       1828
Gly Phe Thr Ala Leu Cys Pro Ala Ser Asp Pro Lys Pro Asn Phe Thr
    590                 595                 600 gac tgt aat agg cat aca caa gtg tgc att aat ggg caa tgt gca ggt       1876
Asp Cys Asn Arg His Thr Gln Val Cys Ile Asn Gly Gln Cys Ala Gly
605                 610                 615                 620 tct atc tgt gag aaa tat ggc tta gag gag tgt acg tgt gcc agt tct       1924
Ser Ile Cys Glu Lys Tyr Gly Leu Glu Glu Cys Thr Cys Ala Ser Ser
                625                 630                 635 gat ggc aaa gat gat aaa gaa tta tgc cat gta tgc tgt atg aag aaa       1972
Asp Gly Lys Asp Asp Lys Glu Leu Cys His Val Cys Cys Met Lys Lys
            640                 645                 650 atg gac cca tca act tgt gcc agt aca ggg tct gtg cag tgg agt agg       2020
Met Asp Pro Ser Thr Cys Ala Ser Thr Gly Ser Val Gln Trp Ser Arg
        655                 660                 665 cac ttc agt ggt cga acc atc acc ctg caa cct gga tcc cct tgc aac       2068
His Phe Ser Gly Arg Thr Ile Thr Leu Gln Pro Gly Ser Pro Cys Asn
    670                 675                 680 gat ttt aga ggt tac tgt gat gtt ttc atg cgg tgc aga tta gta gat       2116
Asp Phe Arg Gly Tyr Cys Asp Val Phe Met Arg Cys Arg Leu Val Asp
685                 690                 695                 700 gct gat ggt cct cta gct agg ctt aaa aaa gca att ttt agt cca gag       2164
Ala Asp Gly Pro Leu Ala Arg Leu Lys Lys Ala Ile Phe Ser Pro Glu
                705                 710                 715 ctc tat gaa aac att gct gaa tgg att gtg gct cat tgg tgg gca gta       2212
Leu Tyr Glu Asn Ile Ala Glu Trp Ile Val Ala His Trp Trp Ala Val
            720                 725                 730 tta ctt atg gga att gct ctg atc atg cta atg gct gga ttt att aag       2260
Leu Leu Met Gly Ile Ala Leu Ile Met Leu Met Ala Gly Phe Ile Lys
        735                 740                 745 ata tgc agt gtt cat act cca agt agt aat cca aag ttg cct cct cct       2308
Ile Cys Ser Val His Thr Pro Ser Ser Asn Pro Lys Leu Pro Pro Pro
    750                 755                 760 aaa cca ctt cca ggc act tta aag agg agg aga cct cca cag ccc att       2356
Lys Pro Leu Pro Gly Thr Leu Lys Arg Arg Arg Pro Pro Gln Pro Ile
765                 770                 775                 780 cag caa ccc cag cgt cag cgg ccc cga gag agt tat caa atg gga cac       2404
Gln Gln Pro Gln Arg Gln Arg Pro Arg Glu Ser Tyr Gln Met Gly His
                785                 790                 795 atg aga cgc taactgcagc ttttgccttg gttcttccta gtgcctacaa              2453
Met Arg Arg tgggaaaact tcactccaaa gagaaaccta ttaagtcatc atctccaaac taaaccctca    2513
caagtaacag ttgaagaaaa aatggcaaga gatcatatcc tcagaccagg tggaattact    2573
taaattttaa agcctgaaaa ttccaatttg gggtgggag gtggaaaagg aacccaattt     2633
tcttatgaac agatattttt aacttaatgg cacaaagtct tagaatatta ttatgtgccc    2693
```

-continued

```
cgtgttccct gttcttcgtt gctgcatttt cttcacttgc aggcaaactt ggctctcaat    2753
aaacttttcg                                                           2763
```

<210> SEQ ID NO 4
<211> LENGTH: 799
<212> TYPE: PRT
<213> ORGANISM: Homo sapiens

<400> SEQUENCE: 4

```
Met Val Leu Leu Arg Val Leu Ile Leu Leu Ser Trp Ala Ala Gly
 1               5                  10                  15

Met Gly Gly Gln Tyr Gly Asn Pro Leu Asn Lys Tyr Ile Arg His Tyr
                20                  25                  30

Glu Gly Leu Ser Tyr Asn Val Asp Ser Leu His Gln Lys His Gln Arg
            35                  40                  45

Ala Lys Arg Ala Val Ser His Glu Asp Gln Phe Leu Arg Leu Asp Phe
        50                  55                  60

His Ala His Gly Arg His Phe Asn Leu Arg Met Lys Arg Asp Thr Ser
    65                  70                  75                  80

Leu Phe Ser Asp Glu Phe Lys Val Glu Thr Ser Asn Lys Val Leu Asp
                85                  90                  95

Tyr Asp Thr Ser His Ile Tyr Thr Gly His Ile Tyr Gly Glu Glu Gly
               100                 105                 110

Ser Phe Ser His Gly Ser Val Ile Asp Gly Arg Phe Glu Gly Phe Ile
           115                 120                 125

Gln Thr Arg Gly Gly Thr Phe Tyr Val Glu Pro Ala Glu Arg Tyr Ile
       130                 135                 140

Lys Asp Arg Thr Leu Pro Phe His Ser Val Ile Tyr His Glu Asp Asp
145                 150                 155                 160

Ile Ser Glu Arg Leu Lys Leu Arg Leu Arg Lys Leu Met Ser Leu Glu
               165                 170                 175

Leu Trp Thr Ser Cys Cys Leu Pro Cys Ala Leu Leu His Ser Trp
           180                 185                 190

Lys Lys Ala Val Asn Ser His Cys Leu Tyr Phe Lys Asp Phe Trp Gly
       195                 200                 205

Phe Ser Glu Ile Tyr Tyr Pro His Lys Tyr Gly Pro Gln Gly Gly Cys
   210                 215                 220

Ala Asp His Ser Val Phe Glu Arg Met Arg Lys Tyr Gln Met Thr Gly
225                 230                 235                 240

Val Glu Glu Val Thr Gln Ile Pro Gln Glu Glu His Ala Ala Asn Gly
               245                 250                 255

Pro Glu Leu Leu Arg Lys Arg Thr Thr Ser Ala Glu Lys Asn Thr
           260                 265                 270

Cys Gln Leu Tyr Ile Gln Thr Asp His Leu Phe Lys Tyr Tyr Gly
       275                 280                 285

Thr Arg Glu Ala Val Ile Ala Gln Ile Ser Ser His Val Lys Ala Ile
   290                 295                 300

Asp Thr Ile Tyr Gln Thr Thr Asp Phe Ser Gly Ile Arg Asn Ile Ser
305                 310                 315                 320

Phe Met Val Lys Arg Ile Arg Ile Asn Thr Thr Ala Asp Glu Lys Asp
               325                 330                 335

Pro Thr Asn Pro Phe Arg Phe Pro Asn Ile Ser Val Glu Lys Phe Leu
           340                 345                 350
```

-continued

```
Glu Leu Asn Ser Glu Gln Asn His Asp Asp Tyr Cys Leu Ala Tyr Val
            355                 360                 365

Phe Thr Asp Arg Asp Phe Asp Asp Gly Val Leu Gly Leu Ala Trp Val
    370                 375                 380

Gly Ala Pro Ser Gly Ser Ser Gly Gly Ile Cys Glu Lys Ser Lys Leu
385                 390                 395                 400

Tyr Ser Asp Gly Lys Lys Ser Leu Asn Thr Gly Ile Ile Thr Val
                405                 410                 415

Gln Asn Tyr Gly Ser His Val Pro Pro Lys Val Ser His Ile Thr Phe
                420                 425                 430

Ala His Glu Val Gly His Asn Phe Gly Ser Pro His Asp Ser Gly Thr
            435                 440                 445

Glu Cys Thr Pro Gly Glu Ser Lys Asn Leu Gly Gln Lys Glu Asn Gly
    450                 455                 460

Asn Tyr Ile Met Tyr Ala Arg Ala Thr Ser Gly Asp Lys Leu Asn Asn
465                 470                 475                 480

Asn Lys Phe Ser Leu Cys Ser Ile Arg Asn Ile Ser Gln Val Leu Glu
                485                 490                 495

Lys Lys Arg Asn Asn Cys Phe Val Glu Ser Gly Gln Pro Ile Cys Gly
            500                 505                 510

Asn Gly Met Val Glu Gln Gly Glu Glu Cys Asp Cys Gly Tyr Ser Asp
        515                 520                 525

Gln Cys Lys Asp Glu Cys Cys Phe Asp Ala Asn Gln Pro Glu Gly Arg
    530                 535                 540

Lys Cys Lys Leu Lys Pro Gly Lys Gln Cys Ser Pro Ser Gln Gly Pro
545                 550                 555                 560

Cys Cys Thr Ala Gln Cys Ala Phe Lys Ser Lys Ser Glu Lys Cys Arg
                565                 570                 575

Asp Asp Ser Asp Cys Ala Arg Glu Gly Ile Cys Asn Gly Phe Thr Ala
            580                 585                 590

Leu Cys Pro Ala Ser Asp Pro Lys Pro Asn Phe Thr Asp Cys Asn Arg
    595                 600                 605

His Thr Gln Val Cys Ile Asn Gly Gln Cys Ala Gly Ser Ile Cys Glu
    610                 615                 620

Lys Tyr Gly Leu Glu Glu Cys Thr Cys Ala Ser Ser Asp Gly Lys Asp
625                 630                 635                 640

Asp Lys Glu Leu Cys His Val Cys Cys Met Lys Lys Met Asp Pro Ser
                645                 650                 655

Thr Cys Ala Ser Thr Gly Ser Val Gln Trp Ser Arg His Phe Ser Gly
            660                 665                 670

Arg Thr Ile Thr Leu Gln Pro Gly Ser Pro Cys Asn Asp Phe Arg Gly
            675                 680                 685

Tyr Cys Asp Val Phe Met Arg Cys Arg Leu Val Asp Ala Asp Gly Pro
            690                 695                 700

Leu Ala Arg Leu Lys Lys Ala Ile Phe Ser Pro Glu Leu Tyr Glu Asn
705                 710                 715                 720

Ile Ala Glu Trp Ile Val Ala His Trp Trp Ala Val Leu Leu Met Gly
                725                 730                 735

Ile Ala Leu Ile Met Leu Met Ala Gly Phe Ile Lys Ile Cys Ser Val
            740                 745                 750

His Thr Pro Ser Ser Asn Pro Lys Leu Pro Pro Pro Lys Pro Leu Pro
    755                 760                 765
```

```
Gly Thr Leu Lys Arg Arg Arg Pro Pro Gln Pro Ile Gln Gln Pro Gln
    770                 775                 780

Arg Gln Arg Pro Arg Glu Ser Tyr Gln Met Gly His Met Arg Arg
785                 790                 795

<210> SEQ ID NO 5
<211> LENGTH: 239
<212> TYPE: DNA
<213> ORGANISM: Homo sapiens

<400> SEQUENCE: 5
aataccacca ttctctgtta tcctgagtat gtcaattaaa cagtaatttt taattaagag      60
cggaaaaatt ttataataca agaaacatc catattgcaa tttctgttta caattgcaca     120
cagaagtaca gtgtacgtaa gaaatacatg tctgcatata acaaggtatg tacattggca     180
agtgatgtct ccaatgttga ggtggtcgag cctcctagcc ttgattggca gttgaaaaa      239

<210> SEQ ID NO 6
<211> LENGTH: 239
<212> TYPE: DNA
<213> ORGANISM: Homo sapiens

<400> SEQUENCE: 6
tttttcaact gccaatcaag gctaggaggc tcgaccacct caacattgga gacatcactt      60
gccaatgtac ataccttgtt atatgcagac atgtatttct tacgtacact gtacttctgt     120
gtgcaattgt aaacagaaat tgcaatatgg atgtttcttt gtattataaa attttttccgc    180 tcttaattaa aaattactgt ttaattgaca tactcaggat aacagagaat ggtggtatt     239

<210> SEQ ID NO 7
<211> LENGTH: 736
<212> TYPE: DNA
<213> ORGANISM: Homo sapiens

<400> SEQUENCE: 7
aaccacttcc aggcacttta aagaggagga gacctccaca gcccattcag caacccagc      60 gtcagcggcc ccgagagagt tatcaaatgg gacacatgag acgctaactg cagcttttgc    120
cttggttctt cctagtgcct acaatgggaa aacttcactc caaagagaaa cctattaagt    180
catcatctcc aaactaaacc ctcacaagta acagttgaag aaaaaatggc aagagatcat    240
atcctcagac caggtggaat tacttaaatt ttaaagcctg aaaattccaa tttgggggtg    300
ggaggtggaa aaggaaccca attttcttat gaacagatat ttttaactta atggcacaaa    360
gtcttagaat attattatgt gccccgtgtt ccctgttctt cgttgctgca ttttcttcac    420
ttgcaggcaa acttggctct caataaactt ttaccacaaa ttgaaataaa tatatttttt    480
tcaactgcca atcaaggcta ggaggctcga ccacctcaac attggagaca atcacttgcc    540
aatgtacata ccttgttata tgcagacatg tatttcttac gtacactgta cttctgtgtg    600
caattgtaaa cagaaattgc aatatggatg tttctttgta ttataaaatt tttccgctct    660
taattaaaaa ttactgttta attgacatac tcaggataac agagaatggt ggtattcagt    720
ggttcagaca caggct                                                     736

<210> SEQ ID NO 8
<211> LENGTH: 2625
<212> TYPE: DNA
<213> ORGANISM: Homo sapiens
```

```
<220> FEATURE:
<221> NAME/KEY: CDS
<222> LOCATION: (17)..(2260)

<400> SEQUENCE: 8
ggcggcggca cggaag atg gtg ttg ctg aga gtg tta att ctg ctc ctc tcc          52
                Met Val Leu Leu Arg Val Leu Ile Leu Leu Leu Ser
                  1               5                  10 tgg gcg gcg ggg atg gga ggt cag tat ggg aat cct tta aat aaa tat          100
Trp Ala Ala Gly Met Gly Gly Gln Tyr Gly Asn Pro Leu Asn Lys Tyr
         15                  20                  25 atc aga cat tat gaa gga tta tct tac aat gtg gat tca tta cac caa          148
Ile Arg His Tyr Glu Gly Leu Ser Tyr Asn Val Asp Ser Leu His Gln
 30                  35                  40 aaa cac cag cgt gcc aaa aga gca gtc tca cat gaa gac caa ttt tta          196
Lys His Gln Arg Ala Lys Arg Ala Val Ser His Glu Asp Gln Phe Leu
 45                  50                  55                  60 cgt cta gat ttc cat gcc cat gga aga cat ttc aac cta cga atg aag          244
Arg Leu Asp Phe His Ala His Gly Arg His Phe Asn Leu Arg Met Lys
             65                  70                  75 agg gac act tcc ctt ttc agt gat gaa ttt aaa gta gaa aca tca aat          292
Arg Asp Thr Ser Leu Phe Ser Asp Glu Phe Lys Val Glu Thr Ser Asn
                 80                  85                  90 aaa gta ctt gat tat gat acc tct cat att tac act gga cat att tat          340
Lys Val Leu Asp Tyr Asp Thr Ser His Ile Tyr Thr Gly His Ile Tyr
                 95                 100                 105 ggt gaa gaa gga agt ttt agc cat ggg tct gtt att gat gga aga ttt          388
Gly Glu Glu Gly Ser Phe Ser His Gly Ser Val Ile Asp Gly Arg Phe
        110                 115                 120 gaa gga ttc atc cag act cgt ggt ggc aca ttt tat gtt gag cca gca          436
Glu Gly Phe Ile Gln Thr Arg Gly Gly Thr Phe Tyr Val Glu Pro Ala
125                 130                 135                 140 gag aga tat att aaa gac cga act ctg cca ttt cac tct gtc att tat          484
Glu Arg Tyr Ile Lys Asp Arg Thr Leu Pro Phe His Ser Val Ile Tyr
                145                 150                 155 cat gaa gat gat att aac tat ccc cat aaa tac ggt cct cag ggc ggc          532
His Glu Asp Asp Ile Asn Tyr Pro His Lys Tyr Gly Pro Gln Gly Gly
                160                 165                 170 tgt gca gat cat tca gta ttt gaa aga atg agg aaa tac cag atg act          580
Cys Ala Asp His Ser Val Phe Glu Arg Met Arg Lys Tyr Gln Met Thr
        175                 180                 185 ggt gta gag gaa gta aca cag ata cct caa gaa gaa cat gct gct aat          628
Gly Val Glu Glu Val Thr Gln Ile Pro Gln Glu Glu His Ala Ala Asn
        190                 195                 200 ggt cca gaa ctt ctg agg aaa aga cgt aca act tca gct gaa aaa aat          676
Gly Pro Glu Leu Leu Arg Lys Arg Arg Thr Thr Ser Ala Glu Lys Asn
205                 210                 215                 220 act tgt cag ctt tat att cag act gat cat ttg ttc ttt aaa tat tac          724
Thr Cys Gln Leu Tyr Ile Gln Thr Asp His Leu Phe Phe Lys Tyr Tyr
                225                 230                 235 gga aca cga gaa gct gtg att gcc cag ata tcc agt cat gtt aaa gcg          772
Gly Thr Arg Glu Ala Val Ile Ala Gln Ile Ser Ser His Val Lys Ala
            240                 245                 250 att gat aca att tac cag acc aca gac ttc tcc gga atc cgt aac atc          820
Ile Asp Thr Ile Tyr Gln Thr Thr Asp Phe Ser Gly Ile Arg Asn Ile
        255                 260                 265 agt ttc atg gtg aaa cgc ata aga atc aat aca act gct gat gag aag          868
Ser Phe Met Val Lys Arg Ile Arg Ile Asn Thr Thr Ala Asp Glu Lys
        270                 275                 280
```

```
gac cct aca aat cct ttc cgt ttc cca aat att agt gtg gag aag ttt       916
Asp Pro Thr Asn Pro Phe Arg Phe Pro Asn Ile Ser Val Glu Lys Phe
285                 290                 295                 300 ctg gaa ttg aat tct gag cag aat cat gat gac tac tgt ttg gcc tat       964
Leu Glu Leu Asn Ser Glu Gln Asn His Asp Asp Tyr Cys Leu Ala Tyr
                305                 310                 315 gtc ttc aca gac cga gat ttt gat gat ggc gta ctt ggt ctg gct tgg      1012
Val Phe Thr Asp Arg Asp Phe Asp Asp Gly Val Leu Gly Leu Ala Trp
320                 325                 330 gtt gga gca cct tca gga agc tct gga gga ata tgt gaa aaa agt aaa      1060
Val Gly Ala Pro Ser Gly Ser Ser Gly Gly Ile Cys Glu Lys Ser Lys
            335                 340                 345 ctc tat tca gat ggt aag aag aag tcc tta aac act gga att att act      1108
Leu Tyr Ser Asp Gly Lys Lys Lys Ser Leu Asn Thr Gly Ile Ile Thr
350                 355                 360 gtt cag aac tat ggg tct cat gta cct ccc aaa gtc tct cac att act      1156
Val Gln Asn Tyr Gly Ser His Val Pro Pro Lys Val Ser His Ile Thr
365                 370                 375                 380 ttt gct cac gaa gtt gga cat aac ttt gga tcc cca cat gat tct gga      1204
Phe Ala His Glu Val Gly His Asn Phe Gly Ser Pro His Asp Ser Gly
                385                 390                 395 aca gag tgc aca cca gga gaa tct aag aat ttg ggt caa aaa gaa aat      1252
Thr Glu Cys Thr Pro Gly Glu Ser Lys Asn Leu Gly Gln Lys Glu Asn
            400                 405                 410 ggc aat tac atc atg tat gca aga gca aca tct ggg gac aaa ctt aac      1300
Gly Asn Tyr Ile Met Tyr Ala Arg Ala Thr Ser Gly Asp Lys Leu Asn
                415                 420                 425 aac aat aaa ttc tca ctc tgt agt att aga aat ata agc caa gtt ctt      1348
Asn Asn Lys Phe Ser Leu Cys Ser Ile Arg Asn Ile Ser Gln Val Leu
430                 435                 440 gag aag aag aga aac aac tgt ttt gtt gaa tct ggc caa cct att tgt      1396
Glu Lys Lys Arg Asn Asn Cys Phe Val Glu Ser Gly Gln Pro Ile Cys
445                 450                 455                 460 gga aat gga atg gta gaa caa ggt gaa gaa tgt gat tgt ggc tat agt      1444
Gly Asn Gly Met Val Glu Gln Gly Glu Glu Cys Asp Cys Gly Tyr Ser
                465                 470                 475 gac cag tgt aaa gat gaa tgc tgc ttc gat gca aat caa cca gag gga      1492
Asp Gln Cys Lys Asp Glu Cys Cys Phe Asp Ala Asn Gln Pro Glu Gly
            480                 485                 490 aga aaa tgc aaa ctg aaa cct ggg aaa cag tgc agt cca agt caa ggt      1540
Arg Lys Cys Lys Leu Lys Pro Gly Lys Gln Cys Ser Pro Ser Gln Gly
                495                 500                 505 cct tgt tgt aca gca cag tgt gca ttc aag tca aag tct gag aag tgt      1588
Pro Cys Cys Thr Ala Gln Cys Ala Phe Lys Ser Lys Ser Glu Lys Cys
510                 515                 520 cgg gat gat tca gac tgt gca agg gaa gga ata tgt aat ggc ttc aca      1636
Arg Asp Asp Ser Asp Cys Ala Arg Glu Gly Ile Cys Asn Gly Phe Thr
525                 530                 535                 540 gct ctc tgc cca gca tct gac cct aaa cca aac ttc aca gac tgt aat      1684
Ala Leu Cys Pro Ala Ser Asp Pro Lys Pro Asn Phe Thr Asp Cys Asn
                545                 550                 555 agg cat aca caa gtg tgc att aat ggg caa tgt gca ggt tct atc tgt      1732
Arg His Thr Gln Val Cys Ile Asn Gly Gln Cys Ala Gly Ser Ile Cys
            560                 565                 570 gag aaa tat ggc tta gag gag tgt acg tgt gcc agt tct gat ggc aaa      1780
Glu Lys Tyr Gly Leu Glu Glu Cys Thr Cys Ala Ser Ser Asp Gly Lys
                575                 580                 585 gat gat aaa gaa tta tgc cat gta tgc tgt atg aag aaa atg gac cca      1828
Asp Asp Lys Glu Leu Cys His Val Cys Cys Met Lys Lys Met Asp Pro
590                 595                 600
```

-continued

```
tca act tgt gcc agt aca ggg tct gtg cag tgg agt agg cac ttc agt    1876
Ser Thr Cys Ala Ser Thr Gly Ser Val Gln Trp Ser Arg His Phe Ser
605                 610                 615                 620 ggt cga acc atc acc ctg caa cct gga tcc cct tgc aac gat ttt aga    1924
Gly Arg Thr Ile Thr Leu Gln Pro Gly Ser Pro Cys Asn Asp Phe Arg
                625                 630                 635 ggt tac tgt gat gtt ttc atg cgg tgc aga tta gta gat gct gat ggt    1972
Gly Tyr Cys Asp Val Phe Met Arg Cys Arg Leu Val Asp Ala Asp Gly
            640                 645                 650 cct cta gct agg ctt aaa aaa gca att ttt agt cca gag ctc tat gaa    2020
Pro Leu Ala Arg Leu Lys Lys Ala Ile Phe Ser Pro Glu Leu Tyr Glu
        655                 660                 665 aac att gct gaa tgg att gtg gct cat tgg tgg gca gta tta ctt atg    2068
Asn Ile Ala Glu Trp Ile Val Ala His Trp Trp Ala Val Leu Leu Met
    670                 675                 680 gga att gct ctg atc atg cta atg gct gga ttt att aag ata tgc agt    2116
Gly Ile Ala Leu Ile Met Leu Met Ala Gly Phe Ile Lys Ile Cys Ser
685                 690                 695                 700 gtt cat act cca agt agt aat cca aag ttg cct cct cct aaa cca ctt    2164
Val His Thr Pro Ser Ser Asn Pro Lys Leu Pro Pro Pro Lys Pro Leu
                705                 710                 715 cca ggc act tta aag agg agg aga cct cca cag ccc att cag caa ccc    2212
Pro Gly Thr Leu Lys Arg Arg Arg Pro Pro Gln Pro Ile Gln Gln Pro
            720                 725                 730 cag cgt cag cgg ccc cga gag agt tat caa atg gga cac atg aga cgc    2260
Gln Arg Gln Arg Pro Arg Glu Ser Tyr Gln Met Gly His Met Arg Arg
        735                 740                 745 taactgcagc ttttgccttg gttcttccta gtgcctacaa tgggaaaact tcactccaaa  2320
gagaaaccta ttaagtcatc atctccaaac taaaccctca caagtaacag ttgaagaaaa  2380
aatggcaaga gatcatatcc tcagaccagg tggaattact taaattttaa agcctgaaaa  2440
ttccaatttg ggggtgggag gtggaaaagg aacccaattt tcttatgaac agatatttt   2500 aacttaatgg cacaaagtct tagaatatta ttatgtgccc cgtgttccct gttcttcgtt  2560
gctgcatttt cttcacttgc aggcaaactt ggctctcaat aaacttttac cacaaaaaaa  2620
aaaaa                                                              2625

<210> SEQ ID NO 9
<211> LENGTH: 748
<212> TYPE: PRT
<213> ORGANISM: Homo sapiens

<400> SEQUENCE: 9

Met Val Leu Leu Arg Val Leu Ile Leu Leu Leu Ser Trp Ala Ala Gly
1               5                   10                  15

Met Gly Gly Gln Tyr Gly Asn Pro Leu Asn Lys Tyr Ile Arg His Tyr
            20                  25                  30

Glu Gly Leu Ser Tyr Asn Val Asp Ser Leu His Gln Lys His Gln Arg
        35                  40                  45

Ala Lys Arg Ala Val Ser His Glu Asp Gln Phe Leu Arg Leu Asp Phe
    50                  55                  60

His Ala His Gly Arg His Phe Asn Leu Arg Met Lys Arg Asp Thr Ser
65                  70                  75                  80

Leu Phe Ser Asp Glu Phe Lys Val Glu Thr Ser Asn Lys Val Leu Asp
                85                  90                  95

Tyr Asp Thr Ser His Ile Tyr Thr Gly His Ile Tyr Gly Glu Glu Gly
            100                 105                 110
```

```
Ser Phe Ser His Gly Ser Val Ile Asp Gly Arg Phe Glu Gly Phe Ile
            115                 120                 125

Gln Thr Arg Gly Gly Thr Phe Tyr Val Glu Pro Ala Glu Arg Tyr Ile
        130                 135                 140

Lys Asp Arg Thr Leu Pro Phe His Ser Val Ile Tyr His Glu Asp Asp
145                 150                 155                 160

Ile Asn Tyr Pro His Lys Tyr Gly Pro Gln Gly Gly Cys Ala Asp His
                165                 170                 175

Ser Val Phe Glu Arg Met Arg Lys Tyr Gln Met Thr Gly Val Glu Glu
            180                 185                 190

Val Thr Gln Ile Pro Gln Glu Glu His Ala Ala Asn Gly Pro Glu Leu
        195                 200                 205

Leu Arg Lys Arg Arg Thr Thr Ser Ala Glu Lys Asn Thr Cys Gln Leu
    210                 215                 220

Tyr Ile Gln Thr Asp His Leu Phe Phe Lys Tyr Tyr Gly Thr Arg Glu
225                 230                 235                 240

Ala Val Ile Ala Gln Ile Ser Ser His Val Lys Ala Ile Asp Thr Ile
                245                 250                 255

Tyr Gln Thr Thr Asp Phe Ser Gly Ile Arg Asn Ile Ser Phe Met Val
            260                 265                 270

Lys Arg Ile Arg Ile Asn Thr Thr Ala Asp Glu Lys Asp Pro Thr Asn
        275                 280                 285

Pro Phe Arg Phe Pro Asn Ile Ser Val Glu Lys Phe Leu Glu Leu Asn
    290                 295                 300

Ser Glu Gln Asn His Asp Asp Tyr Cys Leu Ala Tyr Val Phe Thr Asp
305                 310                 315                 320

Arg Asp Phe Asp Asp Gly Val Leu Gly Leu Ala Trp Val Gly Ala Pro
                325                 330                 335

Ser Gly Ser Ser Gly Gly Ile Cys Glu Lys Ser Lys Leu Tyr Ser Asp
            340                 345                 350

Gly Lys Lys Lys Ser Leu Asn Thr Gly Ile Ile Thr Val Gln Asn Tyr
        355                 360                 365

Gly Ser His Val Pro Pro Lys Val Ser His Ile Thr Phe Ala His Glu
    370                 375                 380

Val Gly His Asn Phe Gly Ser Pro His Asp Ser Gly Thr Glu Cys Thr
385                 390                 395                 400

Pro Gly Glu Ser Lys Asn Leu Gly Gln Lys Glu Asn Gly Asn Tyr Ile
                405                 410                 415

Met Tyr Ala Arg Ala Thr Ser Gly Asp Lys Leu Asn Asn Asn Lys Phe
            420                 425                 430

Ser Leu Cys Ser Ile Arg Asn Ile Ser Gln Val Leu Glu Lys Lys Arg
        435                 440                 445

Asn Asn Cys Phe Val Glu Ser Gly Gln Pro Ile Cys Gly Asn Gly Met
    450                 455                 460

Val Glu Gln Gly Glu Glu Cys Asp Cys Gly Tyr Ser Asp Gln Cys Lys
465                 470                 475                 480

Asp Glu Cys Cys Phe Asp Ala Asn Gln Pro Glu Gly Arg Lys Cys Lys
                485                 490                 495
```

```
Leu Lys Pro Gly Lys Gln Cys Ser Pro Ser Gln Gly Pro Cys Cys Thr
            500                 505                 510
Ala Gln Cys Ala Phe Lys Ser Lys Ser Glu Lys Cys Arg Asp Asp Ser
            515                 520                 525
Asp Cys Ala Arg Glu Gly Ile Cys Asn Gly Phe Thr Ala Leu Cys Pro
            530                 535                 540
Ala Ser Asp Pro Lys Pro Asn Phe Thr Asp Cys Asn Arg His Thr Gln
545                 550                 555                 560
Val Cys Ile Asn Gly Gln Cys Ala Gly Ser Ile Cys Glu Lys Tyr Gly
            565                 570                 575
Leu Glu Glu Cys Thr Cys Ala Ser Ser Asp Gly Lys Asp Asp Lys Glu
            580                 585                 590
Leu Cys His Val Cys Cys Met Lys Lys Met Asp Pro Ser Thr Cys Ala
            595                 600                 605
Ser Thr Gly Ser Val Gln Trp Ser Arg His Phe Ser Gly Arg Thr Ile
            610                 615                 620
Thr Leu Gln Pro Gly Ser Pro Cys Asn Asp Phe Arg Gly Tyr Cys Asp
625                 630                 635                 640
Val Phe Met Arg Cys Arg Leu Val Asp Ala Asp Gly Pro Leu Ala Arg
            645                 650                 655
Leu Lys Lys Ala Ile Phe Ser Pro Glu Leu Tyr Glu Asn Ile Ala Glu
            660                 665                 670
Trp Ile Val Ala His Trp Trp Ala Val Leu Leu Met Gly Ile Ala Leu
            675                 680                 685
Ile Met Leu Met Ala Gly Phe Ile Lys Ile Cys Ser Val His Thr Pro
690                 695                 700
Ser Ser Asn Pro Lys Leu Pro Pro Pro Lys Pro Leu Pro Gly Thr Leu
705                 710                 715                 720
Lys Arg Arg Arg Pro Pro Gln Pro Ile Gln Gln Pro Gln Arg Gln Arg
            725                 730                 735
Pro Arg Glu Ser Tyr Gln Met Gly His Met Arg Arg
            740                 745

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence:antisense
      primers useful in PCR, inverse of the 3' terminus
      of SEQ ID NO: 7

<400> SEQUENCE: 10
agcctgtgtc                                                          10

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence:antisense
      primers useful in PCR, inverse of the 3' terminus
      of SEQ ID NO: 7

<400> SEQUENCE: 11
agcctgtgtc tgaaccact                                                19
```